United States Patent
Morriss

(10) Patent No.: US 9,463,068 B2
(45) Date of Patent: Oct. 11, 2016

(54) METHODS AND DEVICES FOR PROTECTING NASAL TURBINATES

(71) Applicant: Acclarent, Inc., Menlo Park, CA (US)

(72) Inventor: John H. Morriss, San Francisco, CA (US)

(73) Assignee: Acclarent, Inc., Irvine, CA (US)

( * ) Notice: Subject to any disclaimer, the term of this patent is extended or adjusted under 35 U.S.C. 154(b) by 280 days.

(21) Appl. No.: 13/920,372

(22) Filed: Jun. 18, 2013

(65) Prior Publication Data

US 2013/0276794 A1 Oct. 24, 2013

Related U.S. Application Data

(62) Division of application No. 11/801,407, filed on May 8, 2007, now Pat. No. 8,485,199.

(51) Int. Cl.
*A61M 29/00* (2006.01)
*A61B 19/00* (2006.01)
*A61B 17/24* (2006.01)

(52) U.S. Cl.
CPC ............... *A61B 19/00* (2013.01); *A61B 17/24* (2013.01); *A61B 90/04* (2016.02); *A61B 2090/0427* (2016.02)

(58) Field of Classification Search
CPC .......... A61F 5/08; A61F 5/056; A61F 5/058; A61F 5/05883; A61F 5/05891; A61B 17/12; A61B 17/24; A61B 17/12022; A61B 17/12099; A61B 17/12104; A61B 2015/1205; A61B 2015/12054; A61B 2015/248; A61M 2210/00; A61M 2210/06; A61M 2210/0681

USPC .............. 606/191, 196, 199; 602/5, 6, 17; 604/48, 104; 623/10
See application file for complete search history.

(56) References Cited

U.S. PATENT DOCUMENTS

| | | |
|---|---|---|
| 446,173 A | 2/1891 | Hancock |
| 504,424 A | 9/1893 | De Pezzer |
| 513,667 A | 1/1894 | Buckingham |
| 705,346 A | 7/1902 | Hamilton |
| 798,775 A | 9/1905 | Forsyte |
| 816,792 A | 4/1906 | Green |
| 1,080,934 A | 12/1913 | Shackleford |
| 1,200,267 A | 10/1916 | Sunnergren |
| 1,650,959 A | 11/1927 | Pitman |

(Continued)

FOREIGN PATENT DOCUMENTS

| | | |
|---|---|---|
| CH | 668188 | 12/1988 |
| CN | 2151720 | 1/1994 |

(Continued)

OTHER PUBLICATIONS

Argon Medical. Maxxim Medical. Ad for Sniper Elite™ Hydrophilic Ni—Ti Alloy Guidewire (2001).

(Continued)

*Primary Examiner* — Ahmed Farah
(74) *Attorney, Agent, or Firm* — Frost Brown Todd LLC

(57) ABSTRACT

Devices and methods are provided which shield at least one turbinate from trauma or damage during sinus surgery that could be caused by direct contact with diagnostic and therapeutic devices. The devices and methods provided are particularly useful for protecting nasal turbinates during FESS and FTIS procedures.

20 Claims, 7 Drawing Sheets

(56) References Cited

U.S. PATENT DOCUMENTS

| | | |
|---|---|---|
| 1,735,519 A | 11/1929 | Vance |
| 1,828,986 A | 10/1931 | Stevens |
| 1,878,671 A | 9/1932 | Cantor |
| 2,201,749 A | 5/1940 | Vandegrift |
| 2,493,326 A | 1/1950 | Trinder |
| 2,525,183 A | 10/1950 | Robison |
| 2,847,997 A | 8/1958 | Tibone |
| 2,899,227 A | 8/1959 | Jeanrenaud |
| 2,906,179 A | 9/1959 | Bower |
| 2,995,832 A | 8/1961 | Alderson |
| 3,009,265 A | 11/1961 | Bexark |
| 3,037,286 A | 6/1962 | Bower |
| 3,173,418 A | 3/1965 | baran |
| 3,347,061 A | 10/1967 | Stuemky |
| 3,376,659 A | 4/1968 | Asin et al. |
| 3,384,970 A | 5/1968 | Avalear |
| 3,393,073 A | 7/1968 | Reutenauer et al. |
| 3,435,826 A | 4/1969 | Fogarty |
| 3,469,578 A | 9/1969 | Bierman |
| 3,481,043 A | 12/1969 | Esch |
| 3,486,539 A | 12/1969 | Jacuzzi |
| 3,506,005 A | 4/1970 | Gilio et al. |
| 3,509,638 A | 5/1970 | Macleod |
| 3,515,888 A | 6/1970 | Lewis |
| 3,527,220 A | 9/1970 | Summers |
| 3,531,868 A | 10/1970 | Stevenson |
| 3,552,384 A | 1/1971 | Pierie et al. |
| 3,624,661 A | 11/1971 | Shebanow |
| 3,731,963 A | 5/1973 | Pond |
| 3,792,391 A | 2/1974 | Ewing |
| 3,800,788 A | 4/1974 | White |
| 3,802,096 A | 4/1974 | Matern |
| 3,804,081 A | 4/1974 | Kinoshita |
| 3,834,394 A | 9/1974 | Hunter et al. |
| 3,850,176 A | 11/1974 | Gottschalk |
| 3,856,000 A | 12/1974 | Chikama |
| 3,859,993 A | 1/1975 | Bitner |
| 3,871,365 A | 3/1975 | Chikama |
| 3,894,538 A | 7/1975 | Richter |
| 3,903,893 A | 9/1975 | Scheer |
| 3,910,617 A | 10/1975 | Scalza et al. |
| 3,921,636 A | 11/1975 | Zaffaroni |
| 3,948,254 A | 4/1976 | Zaffaroni |
| 3,948,262 A | 4/1976 | Zaffaroni |
| 3,967,618 A | 7/1976 | Zaffaroni |
| 3,993,069 A | 11/1976 | Buckles et al. |
| 3,993,072 A | 11/1976 | Zaffaroni |
| 3,993,073 A | 11/1976 | Zaffaroni |
| 4,016,251 A | 4/1977 | Higuchi et al. |
| 4,052,505 A | 10/1977 | Higuchi et al. |
| 4,053,975 A | 10/1977 | Olbrich et al. |
| 4,069,307 A | 1/1978 | Higuchi et al. |
| 4,102,342 A | 7/1978 | Akiyama et al. |
| 4,138,151 A | 2/1979 | Nakao |
| 4,184,497 A | 1/1980 | Kolff et al. |
| 4,198,766 A | 4/1980 | Camin et al. |
| 4,207,890 A | 6/1980 | Mamajek et al. |
| 4,209,919 A | 7/1980 | Kirikae et al. |
| 4,213,095 A | 7/1980 | Falconer |
| 4,217,898 A | 8/1980 | Theeuwes |
| 4,268,115 A | 5/1981 | Slemon et al. |
| 4,299,226 A | 11/1981 | Banka |
| 4,299,227 A | 11/1981 | Lincoff |
| 4,312,353 A | 1/1982 | Shahbabian |
| 4,338,941 A | 7/1982 | Payton |
| D269,204 S | 5/1983 | Trepp |
| 4,388,941 A | 6/1983 | Reidhammer |
| RE31,351 E | 8/1983 | Falconer |
| 4,435,716 A | 3/1984 | Zandbergen |
| 4,437,856 A | 3/1984 | Valli |
| 4,450,150 A | 5/1984 | Sidman |
| 4,459,977 A | 7/1984 | Pizon et al. |
| 4,464,175 A | 8/1984 | Altman et al. |
| 4,471,779 A | 9/1984 | Antoshkiw et al. |
| 4,499,899 A | 2/1985 | Lyons, III |
| 4,554,929 A | 11/1985 | Samson et al. |
| 4,564,364 A | 1/1986 | Zaffaroni et al. |
| 4,571,239 A | 2/1986 | Heyman |
| 4,571,240 A | 2/1986 | Samson et al. |
| 4,581,017 A | 4/1986 | Sahota |
| 4,585,000 A | 4/1986 | Hershenson |
| D283,921 S | 5/1986 | Dyak |
| 4,589,868 A | 5/1986 | Dretler |
| 4,596,528 A | 6/1986 | Lewis et al. |
| D284,892 S | 7/1986 | Glassman |
| 4,603,564 A | 8/1986 | Kleinhany et al. |
| 4,606,346 A | 8/1986 | Berg et al. |
| 4,607,622 A | 8/1986 | Fritch et al. |
| 4,637,389 A | 1/1987 | Heyden |
| 4,639,244 A | 1/1987 | Rizk et al. |
| 4,645,495 A | 2/1987 | Vaillancourt |
| 4,669,469 A | 6/1987 | Gifford, III |
| 4,672,961 A | 6/1987 | Davies |
| 4,675,613 A | 6/1987 | Naegeli et al. |
| 4,691,948 A | 9/1987 | Austin, Jr. et al. |
| 4,708,434 A | 11/1987 | Tsuno |
| 4,708,834 A | 11/1987 | Cohen et al. |
| 4,726,772 A | 2/1988 | Amplatz |
| 4,736,970 A | 4/1988 | McGourty et al. |
| 4,737,141 A | 4/1988 | Spits |
| 4,748,869 A | 6/1988 | Ohtsuka |
| 4,748,969 A | 6/1988 | Wardle |
| 4,748,986 A | 6/1988 | Morrison et al. |
| 4,755,171 A | 7/1988 | Tennant |
| 4,771,776 A | 9/1988 | Powell et al. |
| 4,793,359 A | 12/1988 | Sharrow |
| 4,795,439 A | 1/1989 | Guest |
| 4,796,629 A | 1/1989 | Grayzel |
| 4,803,076 A | 2/1989 | Ranade |
| 4,811,743 A | 3/1989 | Stevens |
| 4,815,478 A | 3/1989 | Buchbinder et al. |
| 4,819,619 A | 4/1989 | Augustine et al. |
| 4,846,186 A | 7/1989 | Box et al. |
| 4,847,258 A | 7/1989 | Sturm et al. |
| 4,851,228 A | 7/1989 | Zentner et al. |
| 4,854,330 A | 8/1989 | Evans, III et al. |
| 4,862,874 A | 9/1989 | Kellner |
| 4,867,138 A | 9/1989 | Kubota et al. |
| 4,883,465 A | 11/1989 | Brennan |
| 4,897,651 A | 1/1990 | DeMonte |
| 4,898,577 A | 2/1990 | Badger et al. |
| 4,917,419 A | 4/1990 | Mora, Jr. et al. |
| 4,917,667 A | 4/1990 | Jackson |
| 4,919,112 A | 4/1990 | Siegmund |
| 4,920,967 A | 5/1990 | Cottonaro et al. |
| 4,925,445 A | 5/1990 | Sakamoto et al. |
| 4,940,062 A | 7/1990 | Hampton et al. |
| 4,943,275 A | 7/1990 | Stricker |
| 4,946,466 A | 8/1990 | Pinchuk et al. |
| 4,961,433 A | 10/1990 | Christian |
| 4,966,163 A | 10/1990 | Kraus et al. |
| 4,984,581 A | 1/1991 | Stice |
| 4,994,033 A | 2/1991 | Shockey et al. |
| 4,998,916 A | 3/1991 | Hammerslag et al. |
| 4,998,917 A | 3/1991 | Gaiser et al. |
| 5,001,825 A | 3/1991 | Halpern |
| 5,002,322 A | 3/1991 | Fukumoto |
| 5,019,075 A | 5/1991 | Spears et al. |
| 5,019,372 A | 5/1991 | Folkman et al. |
| 5,020,514 A | 6/1991 | Heckele |
| 5,021,043 A | 6/1991 | Becker et al. |
| 5,024,650 A | 6/1991 | Hagiwara et al. |
| 5,024,658 A | 6/1991 | Kozlov et al. |
| 5,026,384 A | 6/1991 | Farr et al. |
| 5,030,227 A | 7/1991 | Rosenbluth et al. |
| 5,041,089 A | 8/1991 | Mueller et al. |
| 5,044,678 A | 9/1991 | Detweiler |
| 5,053,007 A | 10/1991 | Euteneuer |
| 5,055,051 A | 10/1991 | Duncan |
| 5,060,660 A | 10/1991 | Gamble et al. |
| 5,067,489 A | 11/1991 | Lind |
| 5,069,226 A | 12/1991 | Tamauchi et al. |
| 5,087,244 A | 2/1992 | Wolinsky et al. |
| 5,087,246 A | 2/1992 | Smith |

(56) References Cited

U.S. PATENT DOCUMENTS

| | | | |
|---|---|---|---|
| 5,090,595 A | 2/1992 | Vandeninck | |
| 5,090,910 A | 2/1992 | Narlo | |
| 5,094,233 A * | 3/1992 | Brennan | 602/6 |
| 5,112,228 A | 5/1992 | Zouras | |
| 5,116,311 A | 5/1992 | Lofstedt | |
| 5,127,393 A | 7/1992 | McFarlin et al. | |
| 5,137,517 A | 8/1992 | Loney et al. | |
| 5,139,510 A | 8/1992 | Goldsmith, III et al. | |
| 5,139,832 A | 8/1992 | Hayashi et al. | |
| D329,496 S | 9/1992 | Wotton | |
| 5,152,747 A | 10/1992 | Oliver | |
| 5,156,595 A | 10/1992 | Adams | |
| 5,163,989 A | 11/1992 | Campbell et al. | |
| 5,167,220 A | 12/1992 | Brown | |
| 5,168,864 A | 12/1992 | Shockey | |
| 5,169,043 A | 12/1992 | Catania | |
| 5,169,386 A | 12/1992 | Becker et al. | |
| 5,171,233 A | 12/1992 | Amplatz et al. | |
| 5,180,368 A | 1/1993 | Garrison | |
| 5,183,470 A | 2/1993 | Wettermann | |
| 5,189,110 A | 2/1993 | Ikematu et al. | |
| 5,195,168 A | 3/1993 | Yong | |
| 5,197,457 A | 3/1993 | Adair | |
| 5,207,695 A | 5/1993 | Trout, III | |
| 5,211,952 A | 5/1993 | Spicer et al. | |
| 5,215,105 A | 6/1993 | Kizelshteyn et al. | |
| 5,221,260 A | 6/1993 | Burns et al. | |
| 5,226,302 A | 7/1993 | Anderson | |
| 5,230,348 A | 7/1993 | Ishibe et al. | |
| 5,236,422 A | 8/1993 | Eplett, Jr. | |
| 5,243,996 A | 9/1993 | Hall | |
| D340,111 S | 10/1993 | Yoshikawa | |
| 5,250,059 A | 10/1993 | Andreas et al. | |
| 5,251,092 A | 10/1993 | Brady et al. | |
| 5,252,183 A | 10/1993 | Shaban et al. | |
| 5,255,679 A | 10/1993 | Imran | |
| 5,256,144 A | 10/1993 | Kraus et al. | |
| 5,263,926 A | 11/1993 | Wilk | |
| 5,264,260 A | 11/1993 | Saab | |
| 5,267,965 A | 12/1993 | Deneiga | |
| 5,270,086 A | 12/1993 | Hamlin | |
| 5,273,052 A | 12/1993 | Kraus et al. | |
| 5,275,593 A | 1/1994 | Easley et al. | |
| 5,286,254 A | 2/1994 | Shapland et al. | |
| 5,290,310 A | 3/1994 | Makower et al. | |
| 5,295,694 A | 3/1994 | Levin | |
| 5,300,085 A | 4/1994 | Yock | |
| 5,304,123 A | 4/1994 | Atala et al. | |
| 5,308,326 A | 5/1994 | Zimmon | |
| 5,313,967 A | 5/1994 | Lieber et al. | |
| 5,314,417 A | 5/1994 | Stephens et al. | |
| 5,315,618 A | 5/1994 | Yoshida | |
| 5,324,306 A | 6/1994 | Makower et al. | |
| 5,333,620 A | 8/1994 | Moutafis et al. | |
| 5,334,167 A | 8/1994 | Cocanower | |
| 5,336,163 A | 8/1994 | DeMane et al. | |
| 5,341,818 A | 8/1994 | Abrams et al. | |
| 5,342,296 A | 8/1994 | Persson et al. | |
| 5,343,865 A | 9/1994 | Gardineer et al. | |
| 5,345,945 A | 9/1994 | Hodgson et al. | |
| 5,346,075 A | 9/1994 | Nichols et al. | |
| 5,346,508 A | 9/1994 | Hastings | |
| 5,348,537 A | 9/1994 | Wiesner et al. | |
| 5,350,396 A | 9/1994 | Eliachar | |
| 5,356,418 A | 10/1994 | Shturman | |
| 5,368,049 A | 11/1994 | Raman et al. | |
| 5,368,558 A | 11/1994 | Nita | |
| 5,368,566 A | 11/1994 | Crocker | |
| 5,372,138 A | 12/1994 | Crowley et al. | |
| 5,372,584 A | 12/1994 | Zink et al. | |
| D355,031 S | 1/1995 | Yoshikawa | |
| 5,386,817 A | 2/1995 | Jones | |
| 5,391,147 A | 2/1995 | Imran et al. | |
| 5,391,179 A | 2/1995 | Mezzoli | |
| 5,402,799 A | 4/1995 | Colon et al. | |
| 5,409,444 A | 4/1995 | Kensey | |
| 5,411,475 A | 5/1995 | Atala et al. | |
| 5,411,476 A | 5/1995 | Abrams et al. | |
| 5,411,477 A | 5/1995 | Saab | |
| 5,415,633 A | 5/1995 | Lazarus | |
| 5,425,370 A | 6/1995 | Vilkomerson | |
| 5,439,446 A | 8/1995 | Barry | |
| 5,441,494 A | 8/1995 | Ortiz | |
| 5,441,497 A | 8/1995 | Narciso, Jr. | |
| 5,450,853 A | 9/1995 | Hastings et al. | |
| 5,451,221 A | 9/1995 | Cho et al. | |
| 5,454,817 A | 10/1995 | Katz | |
| 5,458,572 A | 10/1995 | Campbell et al. | |
| 5,465,717 A | 11/1995 | Imran et al. | |
| 5,465,733 A | 11/1995 | Hinohara et al. | |
| 5,478,565 A | 12/1995 | Geria | |
| 5,486,181 A | 1/1996 | Cohen et al. | |
| 5,496,338 A | 3/1996 | Miyagi et al. | |
| 5,497,783 A | 3/1996 | Urick et al. | |
| 5,507,301 A | 4/1996 | Wasicek et al. | |
| 5,507,725 A | 4/1996 | Savage et al. | |
| 5,507,766 A | 4/1996 | Kugo et al. | |
| 5,512,055 A | 4/1996 | Domb et al. | |
| 5,514,128 A | 5/1996 | Hillsman et al. | |
| 5,519,532 A | 5/1996 | Broome | |
| 5,531,676 A | 7/1996 | Edwards et al. | |
| 5,533,985 A | 7/1996 | Wong | |
| 5,538,008 A | 7/1996 | Crowe | |
| 5,546,964 A | 8/1996 | Stangerup | |
| 5,549,542 A | 8/1996 | Kovalcheck | |
| 5,558,073 A | 9/1996 | Pomeranz et al. | |
| 5,558,652 A | 9/1996 | Henke | |
| 5,562,619 A | 10/1996 | Mirarchi et al. | |
| 5,568,809 A | 10/1996 | Ben-Haim | |
| 5,571,086 A | 11/1996 | Kaplan et al. | |
| 5,578,007 A | 11/1996 | Imran | |
| 5,578,048 A | 11/1996 | Pasqualucci et al. | |
| 5,584,827 A | 12/1996 | Korteweg et al. | |
| 5,591,194 A | 1/1997 | Berthiaume | |
| 5,599,284 A | 2/1997 | Shea | |
| 5,599,304 A | 2/1997 | Shaari | |
| 5,599,576 A | 2/1997 | Opolski | |
| 5,601,087 A | 2/1997 | Gunderson et al. | |
| 5,601,594 A | 2/1997 | Best | |
| 5,607,386 A | 3/1997 | Flam | |
| 5,617,870 A | 4/1997 | Hastings et al. | |
| 5,626,374 A | 5/1997 | Kim | |
| 5,633,000 A | 5/1997 | Grossman et al. | |
| 5,634,908 A | 6/1997 | Loomas | |
| 5,638,819 A | 6/1997 | Manwaring et al. | |
| 5,643,251 A | 7/1997 | Hillsman et al. | |
| 5,645,789 A | 7/1997 | Roucher, Jr. | |
| 5,647,361 A | 7/1997 | Damadian | |
| 5,656,030 A | 8/1997 | Hunjan et al. | |
| 5,662,674 A | 9/1997 | Debbas | |
| 5,664,567 A | 9/1997 | Linder | |
| 5,664,580 A | 9/1997 | Erickson et al. | |
| 5,665,052 A | 9/1997 | Bullard | |
| 5,669,388 A | 9/1997 | Vilkomerson | |
| 5,673,707 A | 10/1997 | Chandrasekaran | |
| 5,676,673 A | 10/1997 | Ferre et al. | |
| 5,679,400 A | 10/1997 | Tuch | |
| 5,682,199 A | 10/1997 | Lankford | |
| 5,685,838 A | 11/1997 | Peters et al. | |
| 5,685,847 A | 11/1997 | Barry | |
| 5,690,373 A | 11/1997 | Luker | |
| 5,693,065 A | 12/1997 | Rains, III | |
| 5,694,945 A | 12/1997 | Ben-Haim | |
| 5,697,159 A | 12/1997 | Linden | |
| 5,700,286 A | 12/1997 | Tartaglia et al. | |
| 5,707,389 A | 1/1998 | Louw et al. | |
| 5,708,175 A | 1/1998 | Loyanagi et al. | |
| 5,711,315 A | 1/1998 | Jerusalmy | |
| 5,713,839 A * | 2/1998 | Shea | 602/17 |
| 5,713,946 A | 2/1998 | Ben-Haim | |
| 5,718,702 A | 2/1998 | Edwards | |
| 5,720,300 A | 2/1998 | Fagan et al. | |
| 5,722,401 A | 3/1998 | Pietroski et al. | |
| 5,722,984 A | 3/1998 | Fischell et al. | |

(56) References Cited

U.S. PATENT DOCUMENTS

| | | |
|---|---|---|
| 5,729,129 A | 3/1998 | Acker |
| 5,730,128 A | 3/1998 | Pomeranz et al. |
| 5,733,248 A | 3/1998 | Adams et al. |
| 5,752,513 A | 5/1998 | Acker et al. |
| 5,762,604 A | 6/1998 | Kieturakis |
| 5,766,158 A | 6/1998 | Opolski |
| 5,775,327 A | 7/1998 | Randolph et al. |
| 5,776,158 A | 7/1998 | Chou |
| 5,779,699 A | 7/1998 | Lipson |
| 5,789,391 A | 8/1998 | Jacobus et al. |
| 5,792,100 A | 8/1998 | Shantha |
| 5,797,878 A | 8/1998 | Bleam |
| 5,803,089 A | 9/1998 | Ferre et al. |
| 5,814,016 A | 9/1998 | Valley et al. |
| 5,819,723 A | 10/1998 | Joseph |
| 5,820,568 A | 10/1998 | Willis |
| 5,824,044 A | 10/1998 | Quiachon et al. |
| 5,824,048 A | 10/1998 | Tuch |
| 5,824,173 A | 10/1998 | Fontirroche et al. |
| 5,827,224 A | 10/1998 | Shippert |
| 5,830,188 A | 11/1998 | Abouleish |
| 5,833,608 A | 11/1998 | Acker |
| 5,833,645 A | 11/1998 | Lieber et al. |
| 5,833,650 A | 11/1998 | Imran |
| 5,833,682 A | 11/1998 | Amplatz et al. |
| 5,836,638 A | 11/1998 | Slocum |
| 5,836,935 A | 11/1998 | Ashton et al. |
| 5,837,313 A | 11/1998 | Ding et al. |
| 5,843,089 A | 12/1998 | Shatjian et al. |
| 5,843,113 A | 12/1998 | High |
| 5,846,259 A | 12/1998 | Berthiaume |
| 5,857,998 A | 1/1999 | Barry |
| 5,862,693 A | 1/1999 | Myers et al. |
| 5,865,767 A | 2/1999 | Frechette et al. |
| 5,872,879 A | 2/1999 | Hamm |
| 5,873,835 A | 2/1999 | Hastings |
| 5,887,467 A | 3/1999 | Butterweck et al. |
| 5,902,247 A | 5/1999 | Coe et al. |
| 5,902,333 A | 5/1999 | Roberts et al. |
| 5,904,701 A | 5/1999 | Daneshvar |
| 5,908,407 A | 6/1999 | Frazee et al. |
| 5,916,193 A | 6/1999 | Stevens et al. |
| 5,928,192 A | 7/1999 | Maahs |
| 5,931,811 A | 8/1999 | Haissaguerre et al. |
| 5,931,818 A | 8/1999 | Werp et al. |
| 5,932,035 A | 8/1999 | Koger et al. |
| 5,935,061 A | 8/1999 | Acker et al. |
| 5,941,816 A | 8/1999 | Barthel et al. |
| D413,629 S | 9/1999 | Wolff et al. |
| 5,947,988 A | 9/1999 | Smith |
| 5,949,929 A | 9/1999 | Hamm |
| 5,954,693 A | 9/1999 | Barry |
| 5,954,694 A | 9/1999 | Sunseri |
| 5,957,842 A | 9/1999 | Littmann et al. |
| 5,968,085 A | 10/1999 | Morris et al. |
| 5,971,975 A | 10/1999 | Mills et al. |
| 5,979,290 A | 11/1999 | Simeone |
| 5,980,503 A | 11/1999 | Chin |
| 5,980,551 A | 11/1999 | Summers et al. |
| 5,984,945 A | 11/1999 | Sirhan |
| 5,985,307 A | 11/1999 | Hanson et al. |
| 5,997,562 A | 12/1999 | Zadno-Azizi et al. |
| 6,006,126 A | 12/1999 | Cosman |
| 6,006,130 A | 12/1999 | Higo et al. |
| 6,007,516 A | 12/1999 | Burbank et al. |
| 6,007,991 A | 12/1999 | Sivaraman et al. |
| 6,010,511 A | 1/2000 | Murphy |
| 6,013,019 A | 1/2000 | Fischell et al. |
| 6,015,414 A | 1/2000 | Werp et al. |
| 6,016,429 A | 1/2000 | Khafizov et al. |
| 6,016,439 A | 1/2000 | Acker |
| 6,019,736 A | 2/2000 | Avellanet et al. |
| 6,019,777 A | 2/2000 | Mackenzie |
| 6,021,340 A | 2/2000 | Randolph et al. |
| 6,022,313 A | 2/2000 | Ginn et al. |
| 6,027,461 A | 2/2000 | Walker et al. |
| 6,027,478 A | 2/2000 | Katz |
| 6,039,699 A | 3/2000 | Viera |
| 6,042,561 A | 3/2000 | Ash et al. |
| 6,048,299 A | 4/2000 | von Hoffmann |
| 6,048,358 A | 4/2000 | Barak |
| 6,053,172 A | 4/2000 | Hovda et al. |
| 6,056,702 A | 5/2000 | Lorenzo |
| 6,059,752 A | 5/2000 | Segal |
| 6,071,233 A | 6/2000 | Ishikawa et al. |
| 6,079,755 A | 6/2000 | Chang |
| 6,080,190 A | 6/2000 | Schwartz |
| 6,083,148 A | 7/2000 | Williams |
| 6,083,188 A | 7/2000 | Becker et al. |
| 6,086,585 A | 7/2000 | Hovda et al. |
| 6,092,846 A | 7/2000 | Fuss et al. |
| 6,093,150 A | 7/2000 | Chandler et al. |
| 6,093,195 A | 7/2000 | Ouchi |
| 6,109,268 A | 8/2000 | Thapliyal et al. |
| 6,113,567 A | 9/2000 | becker |
| 6,117,105 A | 9/2000 | Bresnaham et al. |
| 6,122,541 A | 9/2000 | Cosman et al. |
| 6,123,697 A | 9/2000 | Shippert |
| 6,136,006 A | 10/2000 | Johnson et al. |
| 6,139,510 A | 10/2000 | Palermo |
| 6,142,957 A | 11/2000 | Diamond et al. |
| 6,148,823 A | 11/2000 | Hastings |
| 6,149,213 A | 11/2000 | Sokurenko et al. |
| 6,159,170 A | 12/2000 | Borodulin et al. |
| 6,171,298 B1 | 1/2001 | Matsuura et al. |
| 6,171,303 B1 | 1/2001 | Ben-Haim |
| 6,174,280 B1 | 1/2001 | Oneda et al. |
| 6,176,829 B1 | 1/2001 | Vilkomerson |
| 6,179,788 B1 | 1/2001 | Sullivan |
| 6,179,811 B1 | 1/2001 | Fugoso et al. |
| 6,183,461 B1 | 2/2001 | Matsuura et al. |
| 6,183,464 B1 | 2/2001 | Sharp et al. |
| 6,190,353 B1 | 2/2001 | Makower et al. |
| 6,190,381 B1 | 2/2001 | Olsen et al. |
| 6,193,650 B1 | 2/2001 | Ryan, Jr. |
| 6,195,225 B1 | 2/2001 | Komatsu et al. |
| 6,200,257 B1 | 3/2001 | Winkler |
| 6,206,870 B1 | 3/2001 | Kanner |
| 6,213,975 B1 | 4/2001 | Laksin |
| 6,221,042 B1 | 4/2001 | Adams |
| 6,231,543 B1 | 5/2001 | Hegde et al. |
| 6,234,958 B1 | 5/2001 | Snoke et al. |
| 6,238,364 B1 | 5/2001 | Becker |
| 6,238,391 B1 | 5/2001 | Olsen et al. |
| 6,241,519 B1 | 6/2001 | Sedleemayer |
| 6,249,180 B1 | 6/2001 | Maalej et al. |
| 6,254,550 B1 | 7/2001 | McNamara et al. |
| 6,268,574 B1 | 7/2001 | Edens |
| 6,293,957 B1 | 9/2001 | Peters et al. |
| 6,302,875 B1 | 10/2001 | Makower et al. |
| 6,306,105 B1 | 10/2001 | Rooney et al. |
| 6,306,124 B1 | 10/2001 | Jones et al. |
| D450,382 S | 11/2001 | Nestenborg |
| 6,322,495 B1 | 11/2001 | Snow et al. |
| 6,328,564 B1 | 12/2001 | Thurow |
| 6,332,089 B1 | 12/2001 | Acker et al. |
| 6,332,891 B1 | 12/2001 | Himes |
| 6,340,360 B1 | 1/2002 | Lyles et al. |
| 6,348,041 B1 | 2/2002 | Klint |
| 6,352,503 B1 | 3/2002 | Matsui et al. |
| 6,375,615 B1 | 4/2002 | Flaherty et al. |
| 6,375,629 B1 | 4/2002 | Muni et al. |
| 6,383,146 B1 | 5/2002 | Klint |
| 6,386,197 B1 | 5/2002 | Miller |
| 6,389,313 B1 | 5/2002 | Marchitto et al. |
| 6,390,993 B1 | 5/2002 | Cornish et al. |
| 6,394,093 B1 | 5/2002 | Lethi |
| 6,398,758 B1 | 6/2002 | Jacobsen et al. |
| 6,409,863 B1 | 6/2002 | Williams et al. |
| 6,423,012 B1 | 7/2002 | Kato et al. |
| 6,425,877 B1 | 7/2002 | Edwards |
| 6,432,986 B2 | 8/2002 | Levin |
| 6,440,061 B1 | 8/2002 | Wenner et al. |
| 6,443,947 B1 | 9/2002 | Marko et al. |

(56) References Cited

U.S. PATENT DOCUMENTS

| | | |
|---|---|---|
| 6,445,939 B1 | 9/2002 | Swanson et al. |
| 6,450,975 B1 | 9/2002 | Brennan et al. |
| 6,450,989 B2 | 9/2002 | Dubrul et al. |
| 6,464,650 B2 | 10/2002 | Jafari et al. |
| 6,468,202 B1 | 10/2002 | Irion et al. |
| 6,468,297 B1 | 10/2002 | Williams et al. |
| 6,485,475 B1 | 11/2002 | Chelly |
| 6,491,940 B1 | 12/2002 | Levin |
| 6,494,894 B2 | 12/2002 | Mirarchi |
| 6,500,130 B2 | 12/2002 | Kinsella et al. |
| 6,500,189 B1 | 12/2002 | Lang et al. |
| 6,503,087 B1 | 1/2003 | Eggert et al. |
| 6,503,185 B1 | 1/2003 | Waksman et al. |
| 6,503,263 B2 | 1/2003 | Adams |
| 6,511,418 B2 | 1/2003 | Shahidi et al. |
| 6,514,249 B1 | 2/2003 | Maguire et al. |
| 6,517,478 B2 | 2/2003 | Khadem |
| 6,524,129 B2 | 2/2003 | Cote et al. |
| 6,524,299 B1 | 2/2003 | Tran et al. |
| 6,526,302 B2 | 2/2003 | Hassett |
| 6,527,753 B2 | 3/2003 | Sekine et al. |
| 6,529,756 B1 | 3/2003 | Phan et al. |
| 6,533,754 B1 | 3/2003 | Hisamatsu et al. |
| 6,536,437 B1 | 3/2003 | Dragisic |
| 6,537,294 B1 | 3/2003 | Boyle et al. |
| 6,543,452 B1 | 4/2003 | Lavigne |
| 6,544,230 B1 | 4/2003 | Flaherty et al. |
| 6,549,800 B1 | 4/2003 | Atalar et al. |
| 6,551,239 B2 | 4/2003 | Renner et al. |
| 6,569,146 B1 | 5/2003 | Werner et al. |
| 6,569,147 B1 | 5/2003 | Evans et al. |
| 6,571,131 B1 | 5/2003 | Nguyen |
| 6,572,538 B2 | 6/2003 | Takase |
| 6,572,590 B1 | 6/2003 | Stevens et al. |
| 6,579,285 B2 | 6/2003 | Sinofsky |
| 6,585,639 B1 | 7/2003 | Kotmel et al. |
| 6,585,717 B1 | 7/2003 | Wittenberger et al. |
| 6,585,794 B2 | 7/2003 | Shimoda et al. |
| 6,589,237 B2 | 7/2003 | Woloszko et al. |
| 6,591,130 B2 | 7/2003 | Shahidi |
| 6,596,009 B1 | 7/2003 | Jelic |
| 6,607,546 B1 | 8/2003 | Murken |
| 6,612,999 B2 | 9/2003 | Brennan et al. |
| 6,613,066 B1 | 9/2003 | Fukaya et al. |
| 6,616,601 B2 | 9/2003 | Hayakawa |
| 6,616,659 B1 | 9/2003 | de la Torre et al. |
| 6,616,678 B2 | 9/2003 | Nishtala et al. |
| 6,616,913 B1 | 9/2003 | Mautone |
| 6,619,085 B1 | 9/2003 | Hsieh |
| 6,634,684 B2 | 10/2003 | Spiessl |
| 6,638,233 B2 | 10/2003 | Corvi et al. |
| 6,638,268 B2 | 10/2003 | Niazi |
| 6,638,291 B1 | 10/2003 | Ferrera et al. |
| 6,645,193 B2 | 11/2003 | Mangosong |
| 6,652,472 B2 | 11/2003 | Jafari et al. |
| 6,652,480 B1 | 11/2003 | Imran et al. |
| 6,656,166 B2 | 12/2003 | Lurie et al. |
| 6,663,589 B1 | 12/2003 | Halevy |
| 6,669,689 B2 | 12/2003 | Lehmann et al. |
| 6,669,711 B1 | 12/2003 | Noda |
| 6,672,773 B1 | 1/2004 | Glenn et al. |
| 6,673,025 B1 | 1/2004 | Richardson et al. |
| 6,679,871 B2 | 1/2004 | Hahnen |
| 6,685,648 B2 | 2/2004 | Flaherty et al. |
| 6,689,096 B1 | 2/2004 | Loubens et al. |
| 6,689,146 B1 | 2/2004 | Himes |
| 6,702,735 B2 | 3/2004 | Kelly |
| 6,712,757 B2 | 3/2004 | Becker et al. |
| 6,714,809 B2 | 3/2004 | Lee et al. |
| 6,716,183 B2 | 4/2004 | Clayman et al. |
| 6,716,216 B1 | 4/2004 | Boucher et al. |
| 6,716,813 B2 | 4/2004 | Lim et al. |
| 6,719,749 B1 | 4/2004 | Schweikert et al. |
| 6,719,763 B2 | 4/2004 | Chung et al. |
| 6,726,701 B2 | 4/2004 | Gilson et al. |
| 6,755,812 B2 | 6/2004 | Peterson et al. |
| 6,776,772 B1 | 8/2004 | de Vrijer et al. |
| 6,780,168 B2 | 8/2004 | Jellie |
| 6,783,522 B2 | 8/2004 | Fischell |
| 6,783,536 B2 | 8/2004 | Vilsmeier et al. |
| 6,786,864 B2 | 9/2004 | Matsuura et al. |
| 6,796,960 B2 | 9/2004 | Cioanta et al. |
| 6,811,544 B2 | 11/2004 | Schaer |
| 6,817,364 B2 | 11/2004 | Garibaldi et al. |
| 6,817,976 B2 | 11/2004 | Rovengo |
| 6,827,683 B2 | 12/2004 | Otawara |
| 6,827,701 B2 | 12/2004 | MacMahon et al. |
| 6,832,715 B2 | 12/2004 | Eungard et al. |
| D501,677 S | 2/2005 | Becker |
| 6,851,290 B1 | 2/2005 | Meier et al. |
| 6,860,264 B2 | 3/2005 | Christopher |
| 6,860,849 B2 | 3/2005 | Matsushita et al. |
| 6,878,106 B1 | 4/2005 | Herrmann |
| 6,890,329 B2 | 5/2005 | Carroll et al. |
| 6,899,672 B2 | 5/2005 | Chin et al. |
| 6,902,556 B2 | 6/2005 | Grimes et al. |
| 6,913,763 B2 | 7/2005 | Lerner |
| 6,927,478 B2 | 8/2005 | Paek |
| 6,939,361 B1 | 9/2005 | Kleshinski |
| 6,939,374 B2 | 9/2005 | Banik et al. |
| 6,955,657 B1 | 10/2005 | Webler |
| 6,966,906 B2 | 11/2005 | Brown |
| 6,971,998 B2 | 12/2005 | Rosenman et al. |
| 6,979,290 B2 | 12/2005 | Mourlas et al. |
| 6,984,203 B2 | 1/2006 | Tartaglia et al. |
| 6,991,597 B2 | 1/2006 | Gellman et al. |
| 6,997,931 B2 | 2/2006 | Sauer et al. |
| 6,997,941 B2 | 2/2006 | Sharkey et al. |
| 7,004,173 B2 | 2/2006 | Sparks et al. |
| 7,008,412 B2 | 3/2006 | Maginot |
| 7,011,654 B2 | 3/2006 | Dubrul et al. |
| 7,022,105 B1 | 4/2006 | Edwards |
| 7,043,961 B2 | 5/2006 | Pandey |
| 7,052,474 B2 | 5/2006 | Castell et al. |
| 7,056,284 B2 | 6/2006 | Martone et al. |
| 7,056,303 B2 | 6/2006 | Dennis et al. |
| 7,074,197 B2 | 7/2006 | Reynolds et al. |
| 7,074,426 B2 | 7/2006 | Kochinke |
| 7,097,612 B2 | 8/2006 | Bertolero et al. |
| 7,108,677 B2 | 9/2006 | Courtney et al. |
| 7,108,706 B2 | 9/2006 | Hogle |
| 7,128,718 B2 | 10/2006 | Hojeibane et al. |
| 7,131,969 B1 | 11/2006 | Hovda et al. |
| 7,140,480 B2 | 11/2006 | Drussel et al. |
| D534,216 S | 12/2006 | Makower et al. |
| 7,160,255 B2 | 1/2007 | Saadat |
| 7,169,140 B1 | 1/2007 | Kume |
| 7,169,163 B2 | 1/2007 | Becker |
| 7,172,562 B2 | 2/2007 | McKinley |
| 7,174,774 B2 | 2/2007 | Pawar et al. |
| 7,182,735 B2 | 2/2007 | Shireman et al. |
| 7,184,827 B1 | 2/2007 | Edwards |
| 7,214,201 B2 | 5/2007 | Burmeister et al. |
| 7,233,820 B2 | 6/2007 | Gilboa |
| 7,235,099 B1 | 6/2007 | Duncavage et al. |
| 7,237,313 B2 | 7/2007 | Skujins et al. |
| 7,252,677 B2 | 8/2007 | Burwell et al. |
| 7,282,057 B2 | 10/2007 | Surti et al. |
| 7,294,345 B2 | 11/2007 | Haapakumpu et al. |
| 7,294,365 B2 | 11/2007 | Hayakawa et al. |
| 7,313,430 B2 | 12/2007 | Urquhart et al. |
| 7,316,168 B2 | 1/2008 | van der Knokke et al. |
| 7,316,656 B2 | 1/2008 | Shireman et al. |
| 7,318,831 B2 | 1/2008 | Alvarez et al. |
| 7,322,934 B2 | 1/2008 | Miyake et al. |
| 7,326,235 B2 | 2/2008 | Edwards |
| 7,338,467 B2 | 3/2008 | Lutter |
| 7,343,920 B2 | 3/2008 | Toby et al. |
| 7,359,755 B2 | 4/2008 | Jones et al. |
| 7,361,168 B2 | 4/2008 | Makower et al. |
| 7,366,562 B2 | 4/2008 | Dukesherer |
| 7,371,210 B2 | 5/2008 | Brock et al. |
| 7,381,205 B2 | 6/2008 | Thommen |
| 7,410,480 B2 | 8/2008 | Muni et al. |

(56) References Cited

U.S. PATENT DOCUMENTS

| | | |
|---|---|---|
| 7,419,497 B2 | 9/2008 | Muni et al. |
| 7,438,701 B2 | 10/2008 | Theeuwes et al. |
| 7,442,191 B2 | 10/2008 | Hovda et al. |
| 7,452,351 B2 | 11/2008 | Miller et al. |
| 7,454,244 B2 | 11/2008 | Kassab et al. |
| 7,462,175 B2 | 12/2008 | Chang et al. |
| 7,471,994 B2 | 12/2008 | Ford et al. |
| 7,481,218 B2 | 1/2009 | Djupesland |
| 7,481,800 B2 | 1/2009 | Jacques |
| D586,465 S | 2/2009 | Faulkner et al. |
| D586,916 S | 2/2009 | Faulkner et al. |
| 7,488,313 B2 | 2/2009 | Segal et al. |
| 7,488,337 B2 | 2/2009 | Saab et al. |
| 7,493,156 B2 | 2/2009 | Manning et al. |
| 7,500,971 B2 | 3/2009 | Chang et al. |
| D590,502 S | 4/2009 | Geisser et al. |
| 7,520,876 B2 | 4/2009 | Ressemann et al. |
| 7,532,920 B1 | 5/2009 | Ainsworth et al. |
| 7,544,192 B2 | 6/2009 | Eaton et al. |
| 7,559,925 B2 | 7/2009 | Goldfarb et al. |
| 7,610,104 B2 | 10/2009 | Kaplan et al. |
| 7,615,005 B2 | 11/2009 | Stefanchik et al. |
| 7,618,450 B2 | 11/2009 | Zarowski et al. |
| 7,625,335 B2 | 12/2009 | Deichmann et al. |
| 7,632,291 B2 | 12/2009 | Stephens et al. |
| 7,634,233 B2 | 12/2009 | Deng et al. |
| 7,641,644 B2 | 1/2010 | Chang et al. |
| 7,641,668 B2 | 1/2010 | Perry et al. |
| 7,645,272 B2 | 1/2010 | Chang et al. |
| 7,648,367 B1 | 1/2010 | Makower et al. |
| 7,654,997 B2 | 2/2010 | Makower et al. |
| 7,680,244 B2 | 3/2010 | Gertner et al. |
| 7,686,798 B2 | 3/2010 | Eaton et al. |
| 7,691,120 B2 | 4/2010 | Shluzas et al. |
| 7,717,933 B2 | 5/2010 | Becker |
| 7,720,521 B2 | 5/2010 | Chang et al. |
| 7,727,186 B2 | 6/2010 | Makower et al. |
| 7,727,226 B2 | 6/2010 | Chang et al. |
| 7,736,301 B1 | 6/2010 | Webler et al. |
| 7,740,642 B2 | 6/2010 | Becker |
| 7,753,929 B2 | 7/2010 | Becker |
| 7,753,930 B2 | 7/2010 | Becker |
| 7,771,409 B2 | 8/2010 | Chang et al. |
| 7,775,968 B2 | 8/2010 | Mathis |
| 7,799,048 B2 | 9/2010 | Hudson et al. |
| 7,803,150 B2 | 9/2010 | Chang et al. |
| 7,833,282 B2 | 11/2010 | Mandpe |
| 7,837,672 B2 | 11/2010 | Intoccia |
| 7,840,254 B2 | 11/2010 | Glossop |
| 7,854,744 B2 | 12/2010 | Becker |
| D630,321 S | 1/2011 | Hamilton, Jr. |
| 7,875,050 B2 | 1/2011 | Samson et al. |
| D632,791 S | 2/2011 | Murner |
| 7,883,717 B2 | 2/2011 | Varner et al. |
| 7,896,891 B2 | 3/2011 | Catanese, III et al. |
| 7,951,132 B2 | 5/2011 | Eaton et al. |
| 7,988,705 B2 | 8/2011 | Galdonik et al. |
| 7,993,353 B2 | 8/2011 | Roβner et al. |
| 8,002,740 B2 | 8/2011 | Willink et al. |
| 8,014,849 B2 | 9/2011 | Peckham |
| 8,016,752 B2 | 9/2011 | Armstrong et al. |
| 8,025,635 B2 | 9/2011 | Eaton et al. |
| 8,080,000 B2 | 12/2011 | Makower et al. |
| 8,088,063 B2 | 1/2012 | Fujikura et al. |
| 8,088,101 B2 | 1/2012 | Chang et al. |
| 8,090,433 B2 | 1/2012 | Makower et al. |
| 8,100,933 B2 | 1/2012 | Becker |
| 8,104,483 B2 | 1/2012 | Taylor |
| 8,114,062 B2 | 2/2012 | Muni et al. |
| 8,114,113 B2 | 2/2012 | Becker |
| 8,123,722 B2 | 2/2012 | Chang et al. |
| 8,142,422 B2 | 3/2012 | Makower et al. |
| 8,147,545 B2 | 4/2012 | Avior |
| 8,167,821 B2 | 5/2012 | Sharrow |
| 8,190,389 B2 | 5/2012 | Kim et al. |
| 8,197,433 B2 | 6/2012 | Cohen |
| 8,197,552 B2 | 6/2012 | Mandpe |
| 8,249,700 B2 | 8/2012 | Clifford et al. |
| 8,277,386 B2 | 10/2012 | Ahmed et al. |
| 8,317,816 B2 | 11/2012 | Becker |
| 8,337,454 B2 | 12/2012 | Eaton et al. |
| 8,388,642 B2 | 3/2013 | Muni et al. |
| 8,403,954 B2 | 3/2013 | Santin et al. |
| 8,439,687 B1 | 5/2013 | Morriss et al. |
| 8,485,199 B2 | 7/2013 | Morriss |
| 8,535,707 B2 | 9/2013 | Arensdorf et al. |
| 8,585,728 B2 | 11/2013 | Keith et al. |
| 8,585,753 B2 | 11/2013 | Scanlon et al. |
| 8,608,360 B2 | 12/2013 | Nath |
| 8,642,631 B2 | 2/2014 | Anderson et al. |
| 2001/0004644 A1 | 6/2001 | Levin |
| 2001/0034530 A1 | 10/2001 | Malackowski et al. |
| 2002/0006961 A1 | 1/2002 | Katz et al. |
| 2002/0055746 A1 | 5/2002 | Burke et al. |
| 2002/0090388 A1 | 7/2002 | Humes et al. |
| 2003/0013985 A1 | 1/2003 | Saadat |
| 2003/0017111 A1 | 1/2003 | Rabito |
| 2003/0018291 A1 | 1/2003 | Hill et al. |
| 2003/0040697 A1 | 2/2003 | Pass et al. |
| 2003/0083608 A1 | 5/2003 | Evans et al. |
| 2003/0114732 A1 | 6/2003 | Webler et al. |
| 2003/0163154 A1 | 8/2003 | Miyata et al. |
| 2004/0015150 A1 | 1/2004 | Zadno-Azizi |
| 2004/0018980 A1 | 1/2004 | Gurney et al. |
| 2004/0034311 A1 | 2/2004 | Mihakcik |
| 2004/0043052 A1 | 3/2004 | Hunter et al. |
| 2004/0058992 A1 | 3/2004 | Marinello et al. |
| 2004/0064105 A1 | 4/2004 | Capes et al. |
| 2004/0116958 A1 | 6/2004 | Gopferich et al. |
| 2004/0127820 A1 | 7/2004 | Clayman et al. |
| 2004/0158229 A1 | 8/2004 | Quinn |
| 2004/0181175 A1 | 9/2004 | Clayman et al. |
| 2004/0193073 A1 | 9/2004 | DeMello et al. |
| 2004/0230156 A1 | 11/2004 | Schreck et al. |
| 2004/0236231 A1 | 11/2004 | Knighton et al. |
| 2004/0249243 A1 | 12/2004 | Kleiner |
| 2004/0267347 A1 | 12/2004 | Cervantes |
| 2005/0027249 A1 | 2/2005 | Reifart et al. |
| 2005/0055077 A1 | 3/2005 | Marco |
| 2005/0059931 A1 | 3/2005 | Garrison et al. |
| 2005/0089670 A1 | 4/2005 | Large |
| 2005/0107738 A1 | 5/2005 | Slater et al. |
| 2005/0113687 A1 | 5/2005 | Herweck et al. |
| 2005/0113850 A1 | 5/2005 | Tagge |
| 2005/0119590 A1 | 6/2005 | Burmeister et al. |
| 2005/0131316 A1 | 6/2005 | Flagle et al. |
| 2005/0143687 A1 | 6/2005 | Rosenblatt et al. |
| 2005/0182319 A1 | 8/2005 | Glossop |
| 2005/0234507 A1 | 10/2005 | Geske et al. |
| 2005/0244472 A1 | 11/2005 | Hughes et al. |
| 2005/0283221 A1 | 12/2005 | Mann et al. |
| 2006/0004323 A1 | 1/2006 | Chang et al. |
| 2006/0063973 A1 | 3/2006 | Makower et al. |
| 2006/0173382 A1 | 8/2006 | Schreiner |
| 2006/0190022 A1 | 8/2006 | Beyar et al. |
| 2006/0211752 A1 | 9/2006 | Kohn et al. |
| 2006/0271024 A1 | 11/2006 | Gertner et al. |
| 2007/0020196 A1 | 1/2007 | Pipkin et al. |
| 2007/0112358 A1 | 5/2007 | Abbott |
| 2007/0129751 A1 | 6/2007 | Muni et al. |
| 2007/0135789 A1 | 6/2007 | Chang et al. |
| 2007/0167682 A1 | 7/2007 | Goldfarb et al. |
| 2007/0208252 A1 | 9/2007 | Makower |
| 2007/0208301 A1 | 9/2007 | Evard et al. |
| 2007/0249896 A1 | 10/2007 | Goldfarb et al. |
| 2007/0269385 A1 | 11/2007 | Yun et al. |
| 2007/0282305 A1 | 12/2007 | Goldfarb et al. |
| 2007/0293727 A1 | 12/2007 | Goldfarb et al. |
| 2007/0293946 A1 | 12/2007 | Gonzales et al. |
| 2008/0033519 A1 | 2/2008 | Burwell et al. |
| 2008/0051804 A1 | 2/2008 | Cottler et al. |
| 2008/0103521 A1 | 5/2008 | Makower et al. |
| 2008/0119693 A1 | 5/2008 | Makower et al. |
| 2008/0125626 A1 | 5/2008 | Chang et al. |

(56) References Cited

U.S. PATENT DOCUMENTS

| | | |
|---|---|---|
| 2008/0132938 A1 | 6/2008 | Chang et al. |
| 2008/0183128 A1 | 7/2008 | Morriss et al. |
| 2008/0188870 A1 | 8/2008 | Andre et al. |
| 2008/0195041 A1 | 8/2008 | Goldfarb et al. |
| 2008/0228085 A1 | 9/2008 | Jenkins et al. |
| 2008/0262508 A1 | 10/2008 | Clifford et al. |
| 2008/0275483 A1 | 11/2008 | Makower et al. |
| 2008/0281156 A1 | 11/2008 | Makower et al. |
| 2008/0287908 A1 | 11/2008 | Muni et al. |
| 2008/0319424 A1 | 12/2008 | Muni et al. |
| 2009/0030274 A1 | 1/2009 | Goldfarb et al. |
| 2009/0088728 A1 | 4/2009 | Dollar et al. |
| 2009/0156980 A1 | 6/2009 | Eaton et al. |
| 2009/0163890 A1 | 6/2009 | Clifford et al. |
| 2009/0187089 A1 | 7/2009 | Say et al. |
| 2009/0187098 A1 | 7/2009 | Makower et al. |
| 2009/0198216 A1 | 8/2009 | Muni et al. |
| 2009/0240112 A1 | 9/2009 | Goldfarb et al. |
| 2009/0240237 A1 | 9/2009 | Goldfarb et al. |
| 2009/0312745 A1 | 12/2009 | Goldfarb et al. |
| 2010/0030031 A1 | 2/2010 | Goldfarb et al. |
| 2010/0087811 A1 | 4/2010 | Herrin et al. |
| 2010/0114066 A1 | 5/2010 | Makower et al. |
| 2010/0174308 A1 | 7/2010 | Chang et al. |
| 2010/0198191 A1 | 8/2010 | Clifford et al. |
| 2010/0198302 A1 | 8/2010 | Shalev |
| 2010/0274188 A1 | 10/2010 | Chang et al. |

FOREIGN PATENT DOCUMENTS

| | | |
|---|---|---|
| CN | 2352818 | 12/1999 |
| DE | 3202878 | 8/1983 |
| DE | 4032096 | 4/1992 |
| DE | 4406077 | 9/1994 |
| DE | 8810044 | 11/1998 |
| DE | 29923582 | 12/2000 |
| DE | 10104663 | 8/2002 |
| DE | 10105592 | 8/2002 |
| EP | 129634 | 1/1985 |
| EP | 0200430 | 11/1986 |
| EP | 257605 | 3/1988 |
| EP | 355996 | 2/1990 |
| EP | 418391 | 3/1991 |
| EP | 427852 | 5/1991 |
| EP | 623582 | 11/1994 |
| EP | 624349 | 11/1994 |
| EP | 744400 | 11/1996 |
| EP | 585757 | 6/1997 |
| EP | 893426 | 1/1999 |
| EP | 1042998 | 10/2000 |
| EP | 1166710 | 1/2002 |
| EP | 1413258 | 4/2004 |
| EP | 1944053 | 7/2008 |
| FR | 2859377 | 3/2005 |
| FR | 2916144 | 11/2008 |
| GB | 2125874 | 3/1984 |
| GB | 2305174 | 4/1997 |
| JP | S 53-067935 | 6/1978 |
| JP | 10-24098 | 1/1989 |
| JP | 3-503011 | 7/1991 |
| JP | 3-504935 | 10/1991 |
| JP | 4-221313 | 8/1992 |
| JP | 5-211985 | 8/1993 |
| JP | 6-277296 | 10/1994 |
| JP | 7-327916 | 12/1995 |
| JP | 8-317989 | 12/1996 |
| JP | 11-507251 | 6/1999 |
| JP | 2000-501634 | 2/2000 |
| JP | 2001-501846 | 2/2001 |
| JP | 2001-095815 | 4/2001 |
| JP | 2001-526077 | 12/2001 |
| JP | 2002-028166 | 1/2002 |
| JP | 2002-508214 | 3/2002 |
| JP | 2002-537908 | 11/2002 |
| JP | 2002-538850 | 11/2002 |
| JP | 2003-507140 | 2/2003 |
| JP | 2003-062080 | 3/2003 |
| JP | 2003-521327 | 7/2003 |
| JP | 2004-357728 | 12/2004 |
| JP | 2005-532869 | 11/2005 |
| RU | 2213530 | 10/2003 |
| SU | 1662571 | 7/1991 |
| WO | WO 90/11053 | 10/1990 |
| WO | WO 90/14865 | 12/1990 |
| WO | WO 91/17787 | 11/1991 |
| WO | WO 92/15286 | 9/1992 |
| WO | WO 92/22350 | 12/1992 |
| WO | WO 94/12095 | 6/1994 |
| WO | WO 96/29071 | 9/1996 |
| WO | WO 97/21461 | 6/1997 |
| WO | WO 99/24106 | 5/1999 |
| WO | WO 99/30655 | 6/1999 |
| WO | WO 99/32041 | 7/1999 |
| WO | WO 00/09192 | 2/2000 |
| WO | WO 00/23009 | 4/2000 |
| WO | WO 00/51672 | 9/2000 |
| WO | WO 00/53252 | 9/2000 |
| WO | WO 01/45572 | 6/2001 |
| WO | WO 01/54558 | 8/2001 |
| WO | WO 01/56481 | 8/2001 |
| WO | WO 01/70325 | 9/2001 |
| WO | WO 01/74266 | 10/2001 |
| WO | WO 01/97895 | 12/2001 |
| WO | WO 02/062269 | 8/2002 |
| WO | WO 03/049603 | 6/2003 |
| WO | WO 03/063703 | 8/2003 |
| WO | WO 03/105657 | 12/2003 |
| WO | WO 2004/006788 | 1/2004 |
| WO | WO 2004/018980 | 3/2004 |
| WO | WO 2004/026391 | 4/2004 |
| WO | WO 2004/082525 A2 | 9/2004 |
| WO | WO 2004/082525 A3 | 9/2004 |
| WO | WO 2005/018730 | 3/2005 |
| WO | WO 2005/077450 | 8/2005 |
| WO | WO 2005/089670 | 9/2005 |
| WO | WO 2005/117755 | 12/2005 |
| WO | WO 2006/034008 | 3/2006 |
| WO | WO 2006/078884 | 7/2006 |
| WO | WO 2006/107957 | 10/2006 |
| WO | WO 2006/116597 | 11/2006 |
| WO | WO 2006/118737 | 11/2006 |
| WO | WO 2006/135853 | 12/2006 |
| WO | WO 2007/111636 | 10/2007 |
| WO | WO 2007/124260 | 11/2007 |
| WO | WO 2008/036149 | 3/2008 |
| WO | WO 2008/045242 | 4/2008 |
| WO | WO 2008/051918 | 5/2008 |
| WO | WO 2008/134382 | 11/2008 |

OTHER PUBLICATIONS

Aust, R., et al. 'The Functional Size of the Human Maxillary Ostium in Vivo' Acta. Otolaryn. (9178) vol. 78 pp. 432-435.

Baim, D.S., MD 'Grossman's Cardiac Catheterization, Angiography, and Intervention' (2000) Lippincott Williams & Wilkins pp. 76, 84 & 214.

Barrett, S. 'Be Wary of Neurocranial Restructuring (NCR)' Chirobase; Jul. 2003; www.chirobase.org/06DD/ncr.html.

Bartal, N. 'An Improved stent for Use in the Surgical Management of Congenital Posterior Choanal Atresia' J. Laryngol. Otol (1988) vol. 102 pp. 146-147.

Becker, A.E. 'Restenosis After Angioplasty' The Lancet (1988) vol. 331, No. 8584 p. 532.

Bellis, M. History of the Catheter—Balloon Catheter—Thomas Fogarty. Www.inventors.about.com/library/inventors/blcatheter.htm?p=1.

Benninger et al.; Adult Chronic Rhinosinusitis: Defintions, Diagnosis, Epidemiology, and Pathophysiology Arch Otolarygol Head and Neck Surg. vol. 129 Sep. 2003 pp. A1-S32.

Bent et al. 'The Frontal Cell as a Cause of Frontal Sinus Obstruction' American Journal of Rhinology, vol. 8, No. 4 (1994) pp. 185-191.

(56) References Cited

OTHER PUBLICATIONS

Binner et al. 'Fibre-Optic Transillunination of the Sinuses: A Comparison of the Value of Radiography and Transillumination in Antral Disease' Clinical Otolaryngology. vol. 3 (1978) pp. 1-11.
Brown, C.L. et al., 'Safety and Feasibility of Balloon Catheter Dilation of Paranasal Sinus Ostia: A Preliminary Investigation' Annals of Otology, Rhinology & Laryngology (2006) vol. 115, No. 4 pp. 293-299.
Casiano et al. 'Endoscopic Lothrop Procedure: the University of Miami Experience' American Journal of Rhinology, vol. 12, No. 5 (1998) pp. 335-339.
Casserly, I.P. et al., Chapter 7. 'Guides and Wires in Percutaneous Coronary Intervention' Strategic Approaches in Coronary Intervention (2006) Lippincott Williams & Wilkins pp. 91-99.
Chien, Y.W. et al. 'Nasal Systemic Drug Delivery' Drugs and Pharmaceutical Sciences, vol. 39, pp. 60-63.
Cohen et al. 'Endoscopic Sinus Surgery: Where we are and where we're going' Current Opinion in Otolaryngology & Head and Neck Surgery, vol. 13 (2005) pp. 32-38.
Colla, A. et al., 'Trihaloacetylated Enol Ethers—General Synthetic Procedure and Heterocyclic Ring Closure Reactions with Hydroxylamine' Synthesis, Jun. 1991 pp. 483-486.
Costa, M.N. et al. 'Endoscopic Study of the Intranasal Ostium in External Dacryocystorhinostomy Postoperative. Influence of Saline Solution and 5-Flurorouracil' Clinics (2007) vol. 62, Issue1, pp. 41-46.
Cussler, E.L. 'Diffusion: Mass transfer in Fluid Systems' Cambridge University Press (1996).
Davis, G.E. et al. 'A Complication from Neurocranial Restructuring' Arch Otolaryngol Head Neck Surg. vol. 129 Apr. 2003 pp. 472-474.
Deutschmann, R. et al. 'A Contribution to the Topical Treatment of [Maxillary] Sinusitis Preliminary Communication' Stomat DDR 26, (1976) pp. 585-592.
Domb, A. et al. 'Handbook of Biodegradable Polymers' Harwood Academic Publishers (1997).
Doyle Nasal Splints, Jan. 25, 2007; www.doylemedical.com/nasalsplints.htm.
Draf, W. 'Endonasal Micro-Endoscopic Frontal Sinus Surgery: the Fulda Concept' Op Tech Otolaryngol Head Neck Surg. vol. 2 (1991) pp. 234-240.
Edmond, C. et al. 'ENT Surgical Stimulator' Nov. 1989.
ENT Checklist; Physical Examination Performance Checklist [date of publication unknown].
Eremychev, V.A. 'Needles for Puncture and Drainage of the Maxillary Sinus' Meditsinskaya Tekhnika, No. 5 (1974) pp. 54.55.
Feldman, R.L. et al., 'New Steerable, Ultra-Low-Profile, Fixed Wire Angioplasty Catheter: Initial Experience With the Cordis OrionTM Steerable PTCA Balloon Catheter' Cathet. Cardiovasc. Diagn. (1990) vol. 19, No. 2 pp. 142-145.
Ford, C.N. 'A Multipurpose Laryngeal Injector Device' Otolaryngol. Head Neck Surg. (1990) vol. 103, No. 1 pp. 135-137.
Friedman, M., M.D., et al. 'Frontal Sinus Surgery: Endoscopic Technique' Operative Techniques in Otolaryngology—Head and Neck Surgery. vol. 12, No. 2 Jun. 2001 pp. 60-65.
Friedman, et al. 'Intraoperative and Postoperative Assessment of Frontal Sinus Patency by Transillumination' Laryngoscope. vol. 110 Apr. 2000 pp. 683-684.
Friedman, et al 'Middle Turbinate Medialization and Preservation in Endoscopic Surgery' Otolaryngology—Head and Neck Surgery. (2000) vol. 123, No. 1, part 1, pp. 76-80.
Fung, M.K.T. 'Template for Frontal Osteoplastic Flap' Laryngoscope. vol. 96 (1986) pp. 578-579.
Gatot, A. et al. 'Early treatment of Orbital Floor Fractures with Catheter Balloon in Children' Int J. Pediatric Otorhinolaryngol (1991) vol. 21 pp. 97-101.
Gerus, I.I. et al. 'β-Ethoxyvinyl Polyfluroroalkyl Ketones—Versatile Synthones in Fluoroorganic Chemistry' Journal of Fluorine Chemistry. vol. 69 (1994) pp. 195-198. Elesvier Science S.A.

Good, R.H. 'An Intranasal Method for Opening the Frontal Sinus Establishing the Largest Possible Drainage' Laryngoscope. vol. 18 (1908) pp. 266-274.
Gopferich 'Polymer Degradation and Erosion: Mechanisms and Application' Eur. J. Parm. Biophar. vol. 42 (1996) pp. 1-11.
Gorlov, D.V. et al 'Acylation of 2-Methoxypropene with Anhydrides and Halides of Perflurocarboxylic Acids in the Presence of Teriary Amines' Russian Chemical Bulletin. vol. 48 No. 9 Sep. 1999 pp. 1791-1792. Kluwer Academic/Plenum Publishers.
Gottmann, et al. 'Balloon Dilatation in the Nasal Cavity and Paranasal Sinuses' CIRSE. Sep. 25, 2004 pp. 1-27.
Gottmann, et al. 'Balloon Dilatation of Recurrent Ostial Occlusion of the Frontal Sinus' CIRSE Abstract Mar. 2001 B-04353.
Gottman, et al., Balloon Dilatation of Recurrent Ostial Occlusion of the Front Sinus OASIS—Online Abstract Submission and Invitation System, 1996-2006, Coe Truman Technologies, Inc.
Gottmann, et al. 'Successful Treatment of Recurrent Post-Operative Frontal Sinus Stenoses by Balloon Dilatation' CIRSE. Oct. 5, 2002.
Gottmann, D. 'Treatment of Stenoses of Upper Air Routes by Balloon Dilation' Proceeding of the 83rd Annual Convention of Association of West German ENT Physicians (1999).
Gupta, D. et al., 'Dacrystitis Secondary to an Iatrogenic Foreign Body in the Lacrimal Apparatus' Ear, Nose & Throat Journal (2009) www.findarticles.com/p/articles/mi_m0BUM/is_7_88/ai_n32428620/.
Hashim, et al. 'Balloon Compression of the Intermaxillary Sinus for Intractable Post Traumatic Bleeding from the Maxillary Artery' Scandinavian Journal of Plastic and reconstruction Sergery, and Hand Surgery (1999) vol. 33 pp. 321-324.
Hojo, M. et al, 'Electrophilic Substiutions of Olefinic Hydrogens II. Acylation of Vinyle Ethers and N Vinyl Amides Chemistry Letters' (1976) pp. 499-502. Chemical Society of Japan.
Hopf, J.U.G. et al. 'Minature Endoscopes in Otorhinolaryngologic Applications' Min Invas Ther & Allied Technol. (1998) vol. 7, No. 3 pp. 209-218.
Hosemann, W. et al. A Dissection Course on Endoscopic Endonasal Sinus Surgery (2005) Endo-Press, Tuttlingen pp. 4-37.
Hosemann, W. et al. 'Endonasal Frontal Sinusotomy in Surgical Management of Chronic Sinusitis: A Critical Evaluation' American Journal of Rhinology. vol. 11, No. 1 (1997) pp. 1-9.
Hosemann, M.E. et al. 'Experimentelle Untersuchungen sur Wundheilung in den Nasennebenholhlen. II. Spontaner Wundschluss und medikamentose Effekte im standardisierten Wundmodell.' HNO 39 (1991) pp. 48-54. 'Experimental investigations on wound healing of the paranasal sinuses. II. Spontaneous wound closure and pharmacological effects in a standardized animal model.' HNO 39 (1991) pp. 48-54.
Hosemann, W.G. et al. 'Minimally Invasive Endonasal Sinus Surgery' Thieme, Stuttgart, New York (2000).
Hosemann, M.E. et al. 'Normal Wound Healing of the Paranasal Sinuses—Clinical and Experimental Investigations' Eur Arch Otorhinolaryngol. vol. 248, (1991) pp. 390-394.
Hosemann, W. et al. 'Behandlung nach Nasennebenhohleneingriffen, part 2: Theapeutische Maβnahem' HNO akutell 7 (1999) pp. 291-302.
Hospital Corpsman Sickcall Screener's Handbook. Naval Hospital Great Lakes Apr. 1999 www.brooksidepress.org/Products/Operationa.Medicine/DATA. 2001 pp. 1-6.
Hybels, R.L. 'Transillumination Durning Osteoplastic Frontal Sinusotomy' The Laryngoscope. vol. 91 Sep. 1981 pp. 1560.
Ijaduola, T.G.A. 'Use of a Foley Catheter for Short-Tenn Drainage in Frontal Sinus Surgery' Ther Journal of Laryngology and Otology. (1989) vol. 103. pp. 375.378.
Ingals, E.F. 'New Operation and Instruments for Draining the Frontal Sinus' Ann. Otol. Rhinol. Layyngol. vol. 14 (1905) pp. 644-649.
Iro, H. et al., 'A New Device for Frontal Sinus Endoscopy: First Clinical Report' Otolaryngol. Head Neck Surg. (2001) vol. 125 No. 6 pp. 613-616.
Jacobs, J.B. '100 Years of Frontal Sinus Surgery' Laryngoscope. vol. 107 (1997) pp. 1-36.
K-Splint Internal Nasal Splints; Jan. 25, 2007; www.invotec.net/rhinology/ksplint.html.

(56) References Cited

OTHER PUBLICATIONS

Kaiser, H. et al 'Cortizontherapie, Corticoide in Klinik und Praxis' Thieme, Stuggart (1992) pp. 390-401.
Kennedy, D.W., M.D. et al. 'Diseases of the Sinuses: Diagnosis and Management' (Copyright 2001) by B.C. Decker Inc.
Khomutov, S.M. et al. 'Dissolution of a Mixture of Steroids in Cyclodextrin Solutions: a Model Description' Pharmaceutical Chemistry Journal. vol. 35, No. 11 Nov. 2001 pp. 627-629.
Kingdom, T.T. et al. 'Image-Guided Surgery of the Sinuses: Current Technology and Applications' Otolaryngol. Clin. North Am. vol. 37, No. 2 Apr. 2004 pp. 381-400.
Klossek, J.M. et al. 'Local Safety of Intranasal Trimcinolone Acentonide: Clinical and Histological Aspects of Nasal Mucosa in the Long-Term Treatment of Perennial Allergic Rhinitis' Rhinology. vol. 39, No. 1 (2001) pp. 17-22.
Kozlov et al. 'Diagnosis and Treatment of Sinusitis by YAMIK Sinus Catheters' Rhinology (1996) vol. 34, pp. 123-124.
Kuhn, et al. 'The Agger Nasi Cell in Frontal Recess Obstruction: An Anatomic, Radiology and Clinical Correlation' Operative Techniques in Otolaryngology—Head and Neck Surgery. vol. 2, No. 4 (1991) pp. 226-231.
Laliberte, F. et al. 'Clinical and Pathologic Methods to Assess the Long-Term Safety of Nasal Corticosteroids' Allergy. vol. 55, No. 8 (2000) pp. 718-722.
Lang, E.V., et al., 'Access Systems for Puncture at an Acute Angle' J. Vasc. Interv. Radiol. (1995) vol. 6, No. 5 pp. 711-713.
Lanza, D.C. 'Postoperative Care and Avoiding Frontal Recess Stenosis' International Advanced Sinus Symposium Jul. 21-24, 1993.
Large, G.C. 'Crystalline Tetracycline Hydrochloride in the Treatment of Acute and Chronic Maxillary Sinusitis' Canad. M.A.J. (1958) vol. 79 pp. 15-16.
Lund, V.J. 'Maximal Medical Therapy for Chronic Rhinosinusitis' Otolaryngol Clin N. Am. vol. 38 (2005) pp. 1301-1310.
Maran, A.G.D. et al. 'The Use of the Foley Balloon Catheter in the Tripod Fracture' J. Laryngol. Otol. (1971) vol. 85, Issue 9, pp. 897-902.
May, M. et al. 'Frontal Sinus Surgery: Endonasal Drainage Instead of an External Osteopolstic Approach' Op Tech Otolaryngo Head Neck Surgery. 6 (1995) pp. 184-192.
Medtronic, xomed.com—MicroFrance Catalog Browser. Www.xomcat.com/xomfrance/index.php?zone=both&cat=18&sub=58&prodline=1272 Dec. 31, 2003 pp. 1-2.
Mehan, V.K. et al., 'Coronary Angioplasty through 4 French Diagnostic Catheters' Cathet. Cardiovasc. Diagn. (1993) vol. 30, No. 1 pp. 22-26.
Mellor, J.M. et al 'Synthesis of Trifluromethylnaphthalenes' Tetrahedron. vol. 56 (2000) pp. 10067-10074. Elsevier Science Ltd.
Metson, R., et al., 'Endoscopic Treatment of Sphenoid Sinusitis' Otolaryngol. Head Neck Surg. (1996) vol. 114, No. 6 pp. 736-744.
Metson, R. 'Holmium: Yag Laser Endoscopic Sinus Surgery: A Randomized Controlled Study' Laryngoscope. vol. 106, Issue 1, Supplement 77 Jan. 1996 pp. 1-18.
Miller, et al. 'Management of Fractures of the Supraorbital Rim' Journal of Trauma. vol. 18, No. 7 Jul. 1978 pp. 507-512.
Min, Y-G et al. 'Mucociliary Activity and Histopathology of Sinus Mucosa in Experimental Maxilary Sinusitis: A Comparison of Systemic Administration of Antibiotic and Antibiotic Delivery by Polylactic Acid Polymer' Laryngoscope. vol. 105 Aug. 1995 pp. 835-842.
Mols, B. 'Movable Tool Tip for Keyhole Surgery' Delft Outlook, vol. 3 (2005) pp. 13-17.
Mooney, M.R., et al., 'Monorail™ Piccolino Catheter: A New Rapid Exchange/Ultralow Profile Coronary Angioplasty System' Cathet. Cardiovasc. Diagn. (1990) vol. 20, No. 2 pp. 114-119.
Moriguchi, T. et al. 'Additional-Elimination Reaction in the Trifluoroacetylation of Electron-Rich Olefins' J. Org. Chem. vol. 60, No. 11 (1995) pp. 3523.3528. American Chemical Society.
Nasal Surgery and Accessories, Jan. 25, 2007; www.technologyforlife.com.au/ent/nasal.html.

Park, K. et al. 'Biodegradable Hydrogels for Durg Delivery' (1993) Technomic Publishing Inc. Lancaster.
Piccirillo, J.F. et al. 'Physchometric and Clinimetric Validity of the 20-Item Sino-Nasal Outcome test (SNOT-20)' Copyright 1996 Washington University, St. Louis, MO.
Piers, et al. 'A Flexible Distal Tip with Two Degrees of Freedon for Enhanced Dexterity in Endoscopic Robot Surgery' Proceedings 13th Micromechanics Europe Workshop (2002) pp. 271-274.
Podoshin, L et al. 'Balloon Technique for Treatment of Frontal Sinus Fractures' The journal of Laryngology & Otology (1967), vol. 81. pp. 1157-1161.
Pownell, P.H. et al., 'Diagnostic Nasal Endoscopy' plastic & Reconstructive Surgery (1997) vol. 99, Iss5 pp. 1451-1458.
Prince, et al. 'Analysis of the Intranasal Distribution of Ointment' J Otolaryngol. vol. 26 (1997) pp. 357-360.
Ramsdale, D.R., Illustrated Coronary Intervention: A case-oriented approach, (2001) Martin Dunitz Ltd. pp. 1-5.
Ritter, F.N. et al., Atlas of Paranasal Sinus Surgery (1991) Igaku-Shoin Medical Pub. pp. 1-81.
Robison, J. Mathews, M.D. 'Pressure Treatment of Maxillary Sinusitis' J.A.M.A. May 31, 1952 pp. 436-440.
Robison, J. Mathews, M.D. 'Pressure Treatment of Purulent Maxillary Sinusitis' Texas State Journal of Medicine May 1952 pp. 281-288.
St. Croix et al. 'Genes Expressed in Human Tumor Endothelium' Science, vol. 289 May 15, 2000 pp. 1197-1202.
Sama, A., et al., 'Current Opinions on the Surgical Management of Frontal Sinus Disease' ENT News. Www.pinpointmedical.com/ent-news (2009) vol. 17, No. 6 pp. 60-63.
Sanborn, T.A. et al., 'Percutaneous Endocardial Transfer and Expression of Genes to the Myocardium Utilizing Fluropscopic Guidance' Catheter Cardiovasc. Interv. (2001) vol. 52, No. 2 pp. 260-266.
Sawbones Catalog 2001, Pacific Research Laboratories, Inc., Vashon Washington 98070 USA.
Saxon, R.R. et al., 'Technical Aspects of Accessing the Portal Vein During the TIPS Procedure' J. Vasc. Interv. Radiol. (1997) vol. 8, No. 5 pp. 733-744.
Schaefer, S.D., M.D. 'Rhinology and Sinus Disease: A Problem-Oriented Approach' (Copyright 1988) by Mosby, Inc.
Schneider. Pfizer Ad for Softip [date of publication unknown].
Shah, N.J. et al., 'Endoscopic Pituitary Surgery—A Beginner's Guide' Indian Journal of Otolaryngology and Head and Neck Surgery (2004) vol. 56, No. 1 pp. 71-78.
Shah, N.J. 'Functional Endoscopic Sinus Surgery' (1999); found at bhj.org/journal/1999_4104_oct99/sp_659.htm.
Single-Pole and Multi-Pole Lightguides for UV Spot Light Curing Systems.
Sinusitis, Maxillary, Acute Surgical Treatment. Http://www.emedicine.com/ent/topic340,htm. Aug. 29, 2006, pp. 1-11.
Sobol, et al. 'Sinusitis, Maxillary, Acute Surgical Treatment.' eMedicine. Retrieved from the Internet: <<http://emedicine.medscape.com/article/862030-print>> Nov. 16, 2010 pp. 1-11.
Stammberger, H. 'Komplikationen entzundlicher Nasennebenhohlenerkrankungen eischließ iatrogen bedingter Komplikationen' Eur Arch Oti-Rhino-Laryngol Supple. Jan. 1993 pp. 61-102.
Stammberger, et al. Chapter 3 'Special Endoscopic Anatomy of the Lateral Nasal Wall and Ethmoidal Sinuses' Functional Endoscopic Sinus Surgery. (1991) Ch. 3, pp. 49-87.
Strohm, et al. Die Behandlung von Stenosen der oberen Luftwege mittels rontgenologisch gesteuerter Ballondilation Sep. 25, 1999 pp. 1-4.
Strohm, et al 'Le Traitement Des Stenoses Voies Aeriennes Superieures Par Dilation Ay Balloon' Sep. 25, 1999.
Strohm, et al. 'Treatment of Stenoses of the Upper Airways by Balloon Dilation' Sudwestdeutscher Abstract 45 Sep. 25, 1999 pp. 1-3.
SurgTrainer Product Information 2003, Surg Trainer, Ltd. Ibaraki, Japan.
SurgTrainer Product Information 'Incisive Human Nasal Model for ESS Training' Surg Trainer, Ltd. Ibaraki, Japan (2004) www1.accsnet.ne.jp/~juliy/st/en/partslist.html.

(56) References Cited

OTHER PUBLICATIONS

Tabor, M.H. et al., 'Symptomatic Bilateral Duct Cysts in a Newborn—Rhinoscopic Clinic' Ear, Nose & Throat Journal (2003) www.findarticles.com/p/articles/mi_m0BUM/is_2_82/ai_98248244 pp. 1-3.
Tarasov, D.I. et al. 'Application of Drugs Based on Polymers in the Treatment of Acute and Chronic Maxillary Sinusitis' Vestn Otorinoloaringol. vol. 6 (1978) pp. 45-47.
Terumo. Medi-Tech. Boston Scientific. (1993) Ad of Glidewire.
The Operating Theatre Journal (www.otjonline.com) 'Disposable Medical Device for Wound Disclosure/The Tristel Purple Promotion—A Collaboration between Tristel PLC and Karl Storz Ednoscopy (UK) Ltd.' p. 4.
Weber, R. et al. 'Endonasale Stirnhohlenchirugie mit Langzeiteinlage eines Platzhalters' Laryngol. Rhinol. Otol. vol. 76 (1997) pp. 728-734. (English Abstract).
Weber, R. et al., 'Videoendoscopic Analysis of Nasal Steriod Distribution' Rhinology. vol. 37 (1999) pp. 69-73.
Weiner, R.I., D.O., et al., 'Development and Application of Transseptal Left Heart Catheterization' Cathet. Cardiovasc. Diagn. (1988) vol. 15, No. 2, pp. 112-120.
Wiatrak, B.J., et al., 'Unilateral Choanal Atresia: Initial Presentation and Endoscopic Repair' International Journal of Pediatric Otorhinolaryngology (1998) vol. 46, pp. 27-35.
Woog, et al. 'Paranasal Sinus Endoscopy and Orbital Fracture Repair' Arch Ophthalmol. vol. 116 May 1998 pp. 688-691.
Wormald, P.J., et al., 'The 'Swing-Door' Technique for Uncinectomy in Endoscopic Sinus Surgery' The Journal of Laryngology and Otology (1998) vol. 112, pp. 547-551.
Xomed-Treace. Bristol-Myers Squibb. Ad for Laser Shield II. Setting the Standards for Tomorrow. [date of publication unknown].
Yamauchi, Y. et al., 'Development of a Silicone Model for Endoscopic Sinus Surgery' Proc International Journal of Computer Assisted Radiology and Surgery vol. 99 (1999) p. 1039.
Yamauchi, Y., et al., 'A Training System for Endoscopic Sinus Surgery with Skill Evaluation' Computer Assisted Radiology and Surgery (2001) with accompanying poster presentation.
Yanagisawa et al. 'Anterior and Posterior Fontanelles.' Ear, Nose & Throat Journal (2001) vol. 80. pp. 10-12.
Zimarino, M., M.D., et al., 'Initial Experience with the EuropassTM: A new Ultra-Low Profile monorail Balloon Catheter' Cathet. Cardiovasc. Diagn. (1994) vol. 33, No. 1, pp. 76-79.
Australian Office Action, Examiners First Report dated Apr. 8, 2010 for Application No. AU 2005274794.
European Communication dated Sep. 4, 2008 for Application No. EP 05773189.
European Communication dated Jun. 19, 2009 for Application No. EP 05773189.
European Exam Report dated Feb. 22, 2006 for Application No. EP 02716734.5.
European Exam Report dated Feb. 8, 2007 for Application No. EP 02716734.5.
European Search Report and Written Opinion dated Sep. 11, 2009 for Application No. EP 06815174.
European Search Report dated Sep. 27, 2011 for Application No. EP 10182961.
European Search Report dated Sep. 29, 2011 for Application No. EP 10182893.
Partial European Search Report dated Sep. 20, 2007 for Application No. EP 07252018.
Partial European Search Report dated Mar. 25, 2008 for Application No. EP 07252018.
Supplemental Partial European Search Report dated Jun. 2, 2008 for Application No. EP 05773189.
Supplemental Partial European Search Report dated Jul. 1, 2009 for Application No. EP 06815285.
Supplemental Partial European Search Report dated Nov. 19, 2010 for Application No. EP 06751637.
Supplemental European Search Report dated Jan. 29, 2010 for Application No. EP 07836108.
Supplemental European Search Report dated Feb. 2, 2010 for Application No. EP 07836109.
Supplemental European Search Report dated Feb. 17, 2010 for Application No. EP 07836110.
Supplemental European Search Report dated Mar. 1, 2010 for Application No. EP 05778834.
Supplemental European Search Report dated Mar. 16, 2010 for Application No. EP 06718986.
Supplemental European Search Report dated Jun. 22, 2010 for Application No. EP 06784759.
Supplemental European Search Report dated Sep. 23, 2010 for Application No. EP 08746715.
Supplemental European Search Report dated Jan. 28, 2011 for Application No. EP 07777004.
Supplemental European Search Report dated Mar. 31, 2011 for Application No. EP 05798331.
Supplemental European Search Report dated Aug. 30, 2011 for Application No. EP 06800540.
Supplemental European Search Report dated Sep. 29, 2011 for Application No. EP 07750248.
International Preliminary Report on Patentability dated Aug. 7, 2006 for Application No. PCT/US05/25371.
International Preliminary Report on Patentability and Written Opinion dated Sep. 25, 2007 for Application No. PCT/US06/002004.
International Preliminary Report on Patentability dated Feb. 15, 2008 for Application No. PCT/US05/13617.
International Preliminary Report on Patentability and Written Opinion dated Nov. 18, 2008 for Application No. PCT/US07/11449.
International Preliminary Report on Patentability and Written Opinion dated Apr. 7, 2009 for Application No. PCT/US07/021170.
International Preliminary Report on Patentability and Written Opinion dated May 5, 2009 for Application No. PCT/US06/036960.
International Preliminary Report on Patentability and Written Opinion dated Oct. 13, 2009 for Application No. PCT/US08/059786.
International Preliminary Report on Patentability and Written Opinion dated Oct. 27, 2009 for Application No. PCT/US08/061343.
International Preliminary Report on Patentability dated Jun. 29, 2011 for Application No. PCT/US2009/069143.
International Search Report dated Jun. 3, 2002 for Application No. PCT/EP02/01228.
International Search Report and Written Opinion dated Apr. 10, 2006 for Application No. PCT/US05/25371.
International Search Report dated May 8, 2007 for Application No. PCT/US2006/16026.
International Search Report dated Aug. 17, 2007 for Application No. PCT/US05/013617.
International Search Report dated Aug. 29, 2007 for Application No. PCT/US06/002004.
International Search Report dated Sep. 25, 2007 for Application No. PCT/US06/037167.
International Search Report dated Oct. 19, 2007 for Application No. PCT/US07/003394.
International Search Report dated May 29, 2008 for Application No. PCT/US07/021170.
International Search Report dated May 29, 2008 for Application No. PCT/US07/021922.
International Search Report dated Jul. 1, 2008 for Application No. PCT/US06/022745.
International Search Report dated Jul. 3, 2008 for Application No. PCT/US2006/029695.
International Search Report dated Jul. 7, 2008 for Application No. PCT/US07/016213.
International Search Report dated Jul. 8, 2008 for Application No. PCT/US07/011474.
International Search Report dated Jul. 17, 2008 for Application No. PCT/US06/036960.
International Search Report and Written Opinion dated Jul. 21, 2008 for Application No. PCT/US05/033090.
International Search Report dated Aug. 25, 2008 for Application No. PCT/US2008/00091.
International Search Report dated Sep. 10, 2008 for Application No. PCT/US07/016212.

(56) References Cited

OTHER PUBLICATIONS

International Search Report and Written Opinion dated Sep. 12, 2008 for Application No. PCT/US07/16214.
International Search Report and Written Opinion dated Sep. 17, 2008 for Application No. PCT/US08/059786.
International Search Report and Written Opinion dated Sep. 17, 2008 for Application No. PCT/US08/061343.
International Search Report and Written Opinion dated Oct. 1, 2008 for Application No. PCT/US07/011449.
International Search Report dated Oct. 15, 2008 for Application No. PCT/US2008/061048.
International Search Report dated Nov. 30, 2009 for Application No. PCT/US2009/057203.
International Search Report dated Dec. 10, 2009 for Application No. PCT/US2009/052236.
International Search Report dated Dec. 16, 2009 for Application No. PCT/US2009/050800.
International Search Report dated Mar. 31, 2010 for Application No. PCT/US2009/069143.
International Search Report dated Jul. 8, 2010 for Application No. PCT/US2010/027837.
International Search Report and Written Opinion dated Oct. 6, 2010 for Application No. PCT/US2010/040548.
International Search Report dated Mar. 25, 2011 for Application No. PCT/US2010/062161.
International Search Report dated Mar. 28, 2011 for Application No. PCT/US2010/061850.
International Search Report dated Mar. 31, 2011 for Application No. PCT/US2010/060898.
International Search Report dated Mar. 31, 2011 for Application No. PCT/US2009/069143.
International Search Report dated Aug. 9, 2011 for Application No. PCT/US2011/038751.
International Search Report dated May 18, 2012 for Application No. PCT/US2011/052321.
Partial International Search Report dated Feb. 7, 2012 for Application No. PCT/US2011/052321.
USPTO Office Action dated Sep. 16, 2005 for U.S. Appl. No. 10/259,300.
USPTO Office Action dated Jul. 7, 2006 for U.S. Appl. No. 10/259,300.
USPTO Office Action dated Feb. 13, 2007 for U.S. Appl. No. 10/259,300.
USPTO Office Action dated Oct. 9, 2007 for U.S. Appl. No. 10/259,300.
USPTO Office Action dated Jan. 24, 2008 for U.S. Appl. No. 10/259,300.
USPTO Office Action dated Oct. 6, 2008 for U.S. Appl. No. 10/259,300.
USPTO Office Action dated May 29, 2007 for U.S. Appl. No. 10/912,578.
USPTO Office Action dated Nov. 14, 2007 for U.S. Appl. No. 10/912,578.
USPTO Office Action dated Dec. 10, 2007 for U.S. Appl. No. 10/912,578.
USPTO Office Action dated Oct. 18, 2007 for U.S. Appl. No. 11/037,548.
USPTO Office Action dated Dec. 6, 2007 for U.S. Appl. No. 11/037,548.
USPTO Office Action dated Apr. 9, 2008 for U.S. Appl. No. 11/037,548.
USPTO Office Action dated Nov. 28, 2007 for U.S. Appl. No. 11/234,395.
USPTO Office Action dated Sep. 12, 2008 for U.S. Appl. No. 10/829,917.
USPTO Office Action dated Nov. 17, 2008 for U.S. Appl. No. 10/829,917.
USPTO Office Action dated Mar. 18, 2009 for U.S. Appl. No. 10/829,917.
USPTO Office Action dated Nov. 9, 2009 for U.S. Appl. No. 10/829,917.
USPTO Office Action dated Oct. 29, 2008 for U.S. Appl. No. 11/347,147.
USPTO Office Action dated Feb. 4, 2009 for U.S. Appl. No. 11/347,147.
USPTO Office Action dated Aug. 6, 2009 for U.S. Appl. No. 11/347,147.
USPTO Office Action dated Nov. 7, 2008 for U.S. Appl. No. 10/944,270.
USPTO Office Action dated Jan. 28, 2009 for U.S. Appl. No. 10/944,270.
USPTO Office Action dated Apr. 21, 2009 for U.S. Appl. No. 10/944,270.
USPTO Office Action dated Nov. 17, 2008 for U.S. Appl. No. 12/117,582.
USPTO Office Action dated Mar. 3, 2009 for U.S. Appl. No. 12/117,582.
USPTO Office Action dated Aug. 6, 2009 for U.S. Appl. No. 12/117,582.
USPTO Office Action dated Nov. 17, 2008 for U.S. Appl. No. 12/118,931.
USPTO Office Action dated Mar. 4, 2009 for U.S. Appl. No. 12/118,931.
USPTO Office Action dated Jul. 30, 2009 for U.S. Appl. No. 12/118,931.
USPTO Office Action dated Nov. 25, 2008 for U.S. Appl. No. 12/117,961.
USPTO Office Action dated Aug. 6, 2009 for U.S. Appl. No. 12/117,961.
USPTO Office Action dated Dec. 5, 2008 for U.S. Appl. No. 12/120,902.
USPTO Office Action dated Oct. 21, 2009 for U.S. Appl. No. 12/120,902.
USPTO Office Action dated Mar. 17, 2009 for U.S. Appl. No. 11/690,127.
USPTO Office Action dated Mar. 23, 2009 for U.S. Appl. No. 11/804,309.
USPTO Office Action dated Mar. 23, 2009 for U.S. Appl. No. 11/926,326.
USPTO Office Action dated Aug. 28, 2009 for U.S. Appl. No. 11/150,847.
U.S. Appl. No. 60/844,874, filed Sep. 15, 2006.
U.S. Appl. No. 60/922,730, filed Apr. 9, 2007.
U.S. Appl. No. 61/052,413, filed May 12, 2008.
U.S. Appl. No. 61/084,949, filed Jul. 30, 2008.
U.S. Appl. No. 11/789,705, filed Apr. 24, 2007.

\* cited by examiner

METHODS AND DEVICES FOR PROTECTING NASAL TURBINATES

This application is a divisional of U.S. patent application Ser. No. 11/801,407, entitled "Methods and Devices for Protecting Nasal Turbinate During Surgery," filed May 8, 2007, now U.S. Pat. No. 8,485,199, issued Jul. 16, 2013, the disclosure of which is incorporated by reference herein.

FIELD OF THE INVENTION

The present invention relates generally to medical devices and methods and more particularly to methods and devices for protecting nasal turbinates during surgery.

BACKGROUND OF THE INVENTION

The skull contains a series of cavities known as paranasal sinuses that are connected by passageways. The paranasal sinuses include frontal sinuses, ethmoid sinuses, sphenoid sinuses and maxillary sinuses. The paranasal sinuses are lined with mucous-producing mucosal tissue and ultimately open into the nasal cavity. Normally, mucous produced by the mucosal tissue slowly drains out of each sinus through an opening known as an ostium. If the mucosal tissue of one of these passageways becomes inflamed for any reason, the cavities which drain through that passageway can become blocked. This blockage can be periodic (resulting in episodes of pain) or chronic. This interference with drainage of mucous (e.g., occlusion of a sinus ostium) can result in mucosal congestion within the paranasal sinuses. Chronic mucosal congestion of the sinuses can cause damage to the epithelium that lines the sinus with subsequent decreased oxygen tension and microbial growth (e.g., a sinus infection).

The term "sinusitis" refers generally to any inflammation or infection of the paranasal sinuses caused by bacteria, viruses, fungi (molds), allergies or combinations thereof. It has been estimated that chronic sinusitis (e.g., lasting more than 3 months or so) results in 18 million to 22 million physician office visits per year in the United States. Patients who suffer from sinusitis typically experience at least some of the following symptoms: headaches or facial pain; nasal congestion or post-nasal drainage; difficulty breathing through one or both nostrils; bad breath; and/or pain in the upper teeth, One of the ways to treat sinusitis is by restoring the lost mucous flow. The initial therapy is typically drug therapy using anti-inflammatory agents to reduce the inflammation and antibiotics to treat the infection. A large number of patients do not respond to drug therapy. Currently, the gold standard for patients with chronic sinusitis that do not respond to drug therapy is a corrective surgery called Functional Endoscopic Sinus Surgery (FESS).

During FESS, an endoscope is inserted into the nose and, under visualization through the endoscope, the surgeon may remove diseased or hypertrophic tissue or bone and may enlarge the ostia of the sinuses to restore normal drainage of the sinuses. FESS procedures are typically performed with the patient under general anesthesia.

Although FESS continues to be the gold standard therapy for surgical treatment of severe sinus disease, FESS does have several shortcomings. For example, FESS can cause significant post-operative pain. Also, some FESS procedures are associated with significant postoperative bleeding and, as a result, nasal packing is frequently placed in the patient's nose for some period of time following the surgery. Such nasal packing can be uncomfortable and can interfere with normal breathing, eating, drinking etc. Also, some patients remain symptomatic even after multiple FESS surgeries. Additionally, some FESS procedures are associated with risks of iatrogenic orbital, intracranial and sinonasal injury. Many otolaryngologists consider FESS an option only for patients who suffer from severe sinus disease (e.g., those showing significant abnormalities under CT scan). Thus, patients with less severe disease may not be considered candidates for FESS. One of the reasons why FESS procedures can be bloody and painful relates to the fact that instruments having straight, rigid shafts are used. In order to target deep areas of the anatomy with such straight rigid instrumentation, the physician needs to resect and remove or otherwise manipulate any anatomical structures that may lie in the direct path of the instruments, regardless of whether those anatomical structures are part of the pathology.

New devices, systems and techniques are being developed for the treatment of sinusitis and other disorders of the ear, nose, throat and paranasal sinuses. For example, various catheters, guidewires and other devices useable to perform minimally invasive, minimally traumatic ear, nose and throat surgery have been described in U.S. patent applications Ser. No. 10/829,917 entitled "Devices, Systems and Methods for Diagnosing and Treating Sinusitis and Other Disorders of the Ears, Nose and/or Throat," now U.S. Pat. No. 7,654,997, issued Feb. 2, 2010, Ser. No. 10/912,578 entitled "Implantable Device and Methods for Delivering Drugs and Other Substances to Treat Sinusitis and Other Disorders," now U.S. Pat. No. 7,361,168, issued Apr. 22, 2008, Ser. No. 10/944,270 entitled "Apparatus and Methods for Dilating and Modifying Ostia of Paranasal Sinuses and Other Intranasal or Paranasal Structures", now U.S. Pat. Pub. No. 2006/0004323, published Jan. 5, 2006, Ser. No. 11/037,548 entitled "Devices, Systems and Methods For Treating Disorders of the Ear, Nose and Throat", now U.S. Pat. No. 7,462,175, issued Dec. 9, 2008, and Ser. No. 11/116,118 entitled "Methods and Devices For Performing Procedures Within the Ear, Nose, Throat and Paranasal Sinuses", now U.S. Pat. No. 7,720,521, issued May 18, 2010. Each of these applications is hereby incorporated herein, in its entirety, by reference thereto. Many of these new devices, systems and techniques are useable in conjunction with endoscopic, radiographic and/or electronic assistance to facilitate precise positioning and movement of catheters, guidewires and other devices within the ear, nose, throat and paranasal sinuses and to avoid undesirable trauma or damage to critical anatomical structures such as the eyes, facial nerves and brain.

For example, in one new procedure (referred to in this patent application as a "Flexible Transnasal Sinus Intervention" or FTSI), a dilatation catheter (e.g., a balloon catheter or other type of dilator) is advanced through the nose to a position within the ostium of a paranasal sinus or other location, without requiring removal or surgical alteration of other intranasal anatomical structures. The dilatation catheter is then used to dilate the ostium or other anatomical structures to facilitate natural drainage from the sinus cavity. In some cases, a tubular guide may be initially inserted through the nose and advanced to a position near the sinus ostium and a guidewire may then be advanced through the tubular guide and into the affected paranasal sinus. The dilatation catheter may then be advanced over the guidewire and through the tubular guide to a position where its dilator (e.g., balloon) is positioned within the sinus ostium. The dilator (e.g., balloon) is then expanded causing the ostium to dilate. In some cases, such dilatation of the ostium may fracture, move or remodel bony structures that surround or are adjacent to the ostium. Optionally, in some procedures, irrigation solution and/or therapeutic agents may be infused through a lumen of the dilatation catheter and/or other working devices (e.g., guidewires, catheters, cannula, tubes, dilators, balloons, substance injectors, needles, penetrators, cutters, debriders, microdebriders, hemostatic devices, cautery devices, cryosurgical devices, heaters, coolers, scopes, endoscopes, light guides, phototherapy devices, drills, rasps, saws, etc.) may be advanced through the tubular guide and/or over the guidewire to deliver other therapy to the sinus or adjacent tissues during the same procedure in which the FTSI is carried out. In FTSI procedures that include positioning of a guidewire into a paranasal sinus, the placement of the guidewire is typically confirmed by visualizing the procedure under fluoroscopy or other x-ray visualization techniques. It is to be understood that, in FTSI procedures, structures and passageways other than sinus ostia may be dilated using the tools described above, tissue may be resected or ablated, bone may be restructured, drugs or drug delivery systems may be deployed, etc., as described in the documents incorporated herein by reference. Thus, for the purposes of this application the term FTSI will be generally used to refer broadly to all of those procedures, not just dilation of sinus ostia.

A turbinate (or nasal conchae) is a long, narrow and curled bone shelf which protrudes into the breathing passage of the nose. Turbinates divide the nasal airway into three groove-like air passages-and are responsible for forcing inhaled air to flow in a steady, regular pattern around the largest possible surface of cilia and climate controlling tissue. Turbinates are composed of pseudo-stratified columnar ciliated respiratory epithelium with a thick, vascular and erectile glandular tissue layer. The turbinates are located laterally in the nasal cavities, curling medially and downwards into the nasal airway. There are three pairs of turbinates, the superior, middle and inferior turbinate pairs. Each pair is composed of one turbinate in either side of the nasal cavity, divided by the septum.

Aside from being responsible for nasal airflow and required for functional respiration, the turbinates are also responsible for filtration, heating and humidification of air inhaled through the nose. As air passes over the turbinate tissues it is heated to body temperature, humidified and filtered. The respiratory epithelium of the turbinates plays a major role in the body's immmunological defense. The respiratory epithelium of the turbinates are partially composed of goblet cells which secret mucus over the nasal cavities which filters out foreign particals larger than 2 to 3 micrometers. The respiratory epithelium of the turbinates is also involved in the lymphatic system which protects the body from being infected by viruses and/or bacteria.

Both the FESS and FTSI procedures may cause damage to one or more nasal turbinates while navigating the paranasal passageway to and from the surgical target site. Damaging a turbinate may cause pain and/or bleeding which can interfere with the surgical procedure and can also increase the recovery time for the patient.

Some devices have been developed which position a portion of the middle turbinate against the nasal septum prior to endoscopic surgery. This type of nasal splint increases visualization of the nasal cavities to facilitate nasal endoscopic surgery and protects a portion of the middle turbinate from endoscopic tools during surgery by moving or repositioning the middle turbinate against the nasal septum. Unfortunately, these devices require being secured to the nasal septum as well as moving the middle turbinate against the nasal septum which may not be feasible if the turbinate is large or swollen which could lead to blockage of nasal breathing. For examples, see U.S. Pat. No 5,599,284, "Pre-operative nasal splint for endoscopic sinus surgery and method" to Shea, John P, and U.S. Pat. No. 5,713,839, "Pre-operative nasal splint for endoscopic sinus surgery and method" to Shea, John P. Another drawback to these types of splints is that it many not be possible to reposition the turbinate without fracturing it.

Turbinate splints have also been developed and are commonly used as nasal post-operative devices, for example, see U.S. Pat. No. 5,350,396, "Nasal Splint" to Eliachar. These types of splints address particular problems encountered after nasal septal reconstructive surgery. They are usually utilized to support the septum in the correct position during healing and recovery after surgery. Other types of post-operative turbinate splints have been an asset in insuring a more complete separation of the nasal mucosal membranes after surgery or injury, but none of the post-operative nasal splints are configured to be utilized during FESS and FTSI procedures to protect a nasal turbinate from trauma or damage from surgical instruments.

Currently, there are no devices or methods for protecting nasal turbinates, in their natural position, prior to or during sinus surgery. Thus there is a need for methods and devices that can protect nasal turbinates during sinus surgery, and in particular, FESS and FTSI procedures.

SUMMARY OF THE INVENTION

The invention provides apparatus and methods for the protection of nasal turbinates during surgical operations. The apparatus of the invention comprise, in general terms, a first protecting portion; a second protecting portion; and a bridge portion joined to the first and second protecting portions.

In many embodiments the first and second protecting portions each include a proximal end portion, the proximal end portions joined to the bridge portion.

In many embodiments the first protecting portion is structured and configured to protect a first side of a turbinate, the second protecting portion is structured and configured to protect a second side of a turbinate, and the bridge portion is structured and configured to protect an anterior or inferior portion of the turbinate.

In certain embodiments the first and second protecting portions are substantially planar in shape.

In certain embodiments the first and second protecting portions each include a distal end portion, the distal end portions each having a rounded shape, the rounded shapes defining atraumatic surfaces.

In certain embodiments the bridge portion is resilient and the first and second protecting portions are movable with respect to the bridge portion.

In certain embodiments the bridge portion is malleable and the first and second protecting portions are movable with respect to the bridge portion.

In certain embodiments the first and second protecting portions and bridge portions are joined together in a configuration that defines an angle between the first and second protecting portions of between about 25° and about 45°.

In certain embodiments the bridge portion further comprises at least one crease, the crease configured to increase resiliency of the bridge portion.

In certain embodiments the bridge portion further comprises at least one crease, the crease configured to increase malleability of the bridge portion.

In certain embodiments the first and second protecting portions and bridge portion further comprise an inner surface structured and configured to contact a turbinate.

In certain embodiments the inner surface includes a biocompatible adhesive.

In certain embodiments the first and second protecting portions and bridge portion further comprise an outer surface structured and configured to deflect a surgical instrument.

In certain embodiments the first and second protecting portions each include at least one slot structured and configured to facilitate grasping of the first and second portions by a surgical instrument.

In certain embodiments the first and second protecting portions are reversibly movable from or between an open position to a closed position.

In certain embodiments the first and second protecting portions are movable to an open position by application of an opening force to the first and second protecting portions, and movable to a closed position by removal of the opening force from the first and second protecting portions.

In certain embodiments the first and second protecting portions are movable to an open position by application of an opening force to the bridge portion, and movable to a closed position by removal of the opening force from the bridge portion.

In certain embodiments the turbinate protector further comprising a first control element and a second control element, the first and second control elements mechanically coupled to the first and second protecting portion through the bridge portion.

In certain embodiments the first and second control elements are structured and configured such that application of an opening force to the first and second control elements causes the first and second protecting portions to move apart to an open position, and removal of the opening force from the first and second control elements results in the first and second portions moving together to a closed position.

In certain embodiments the first and second control elements are structured and configured such that application of an opening force to the first and second control elements causes distal end portions of the first and second protecting portions to move apart to an open position, and removal of the opening force from the first and second control elements results in the distal end portions of the first and second portions moving together to a closed position.

In certain embodiments the first control element comprises first and second control segments, and the second control element comprises first and second control segments, the first and second control segments of each control element being mechanically coupled to each other.

In certain embodiments the bridge portion is structured and configured such that applying an opening force to the bridge element results in the first and second portions moving apart from each other to an open position, and removing the opening force from the bridge portion results in the first and second portions moving together to a closed position.

In certain embodiments the bridge portion is structured and configured such that applying an opening force to the bridge element results in a distal end portion of the first portion and a distal end portion of the second portion moving apart from each other to an open position, and removing the opening force from the bridge portion results in the distal end portions of the first and second portions moving together to a closed position.

In certain embodiments the bridge portion is arcuate in shape and is joined to the first and second portions by first and second connecting regions, the bridge and connecting regions structured and configured such that applying an opening force to the bridge element results in a distal end portion of the first portion and a distal end portion of the second portion moving apart from each other to an open position, and removing the opening force from the bridge portion results in the distal end portions of the first and second portions moving together to a closed position.

In certain embodiments the turbinate protector further comprises at least one radio-opaque marker thereon.

The invention also provides methods for protecting nasal turbinates during surgical procedures. The methods comprise, in general terms: introducing a turbinate protector into a patient; locating a target turbinate; positioning a turbinate protector on the target turbinate; performing paranasal surgery; and removing the turbinate protector from the patient.

In certain embodiments the introducing of the turbinate protector comprises inserting the turbinate protector through the nasal passage of the patient.

In certain embodiments the locating comprises visualizing the selected or target turbinate via endoscopic imaging.

In certain embodiments the locating comprises visualizing the selected or target turbinate by fluoroscopic imaging utilizing a radio-opaque marker on the turbinate protector.

In certain embodiments the positioning comprises: positioning a first protecting portion of the turbinate protector adjacent to a first side of the turbinate; positioning a second protecting portion of the turbinate protector adjacent to a second side of the turbinate; and positioning a bridge region of the turbinate protector adjacent to the anterior or inferior portion of the turbinate.

In certain embodiments the positioning further comprises contacting the turbinate with an inside surface of the turbinate protector.

In certain embodiments the methods may further comprise securing the inside surface of the turbinate protector to the turbinate with a bioadhesive located on the inner surface.

In certain embodiments the positioning comprises: moving the first and second protecting portions of the turbinate protector to an open position; positioning the target turbinate between the first and second protecting portions; and moving the first and second protecting portions to a closed position.

In certain embodiments the positioning further comprises: applying an opening force to the first and second protecting portions to move the first and second portions to the open position; and removing the opening force from the first and second protecting portions, to move the first and second protecting portions to the closed position.

In certain embodiments the positioning further comprises: applying an opening force to the bridge portion to move the first and second portions to the open position; and removing the opening force from the bridge portion, to move the first and second protecting portions to the closed position.

In certain embodiments the positioning further comprises: positioning the first protecting portion adjacent to a first side of the turbinate; positioning the second protecting portion adjacent to a second side of the turbinate; and positioning the bridge portion adjacent to an anterior or inferior portion of the turbinate.

In certain embodiments the positioning further comprises: applying an opening force to first and second control elements, the first and second control elements being mechanically coupled to the first and second protecting portions; and removing the opening force from the control elements, In certain embodiments the performing paranasal surgery comprises performing FESS surgery.

In certain embodiments the performing paranasal surgery comprises performing FTSI surgery.

In certain embodiments the removing comprises opening the first and second protecting portions; releasing the turbinate from the turbinate protector; and withdrawing the turbinate protector from the patient nasal cavity via the nostril, Further features of the invention will become apparent to those persons skilled in the art upon reading the details of the devices, methods and systems as more fully described below.

DETAILED DESCRIPTION OF THE INVENTION

Before the present devices and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a tube" includes a plurality of such tubes and reference to "the shaft" includes reference to one or more shafts and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Figure 1:
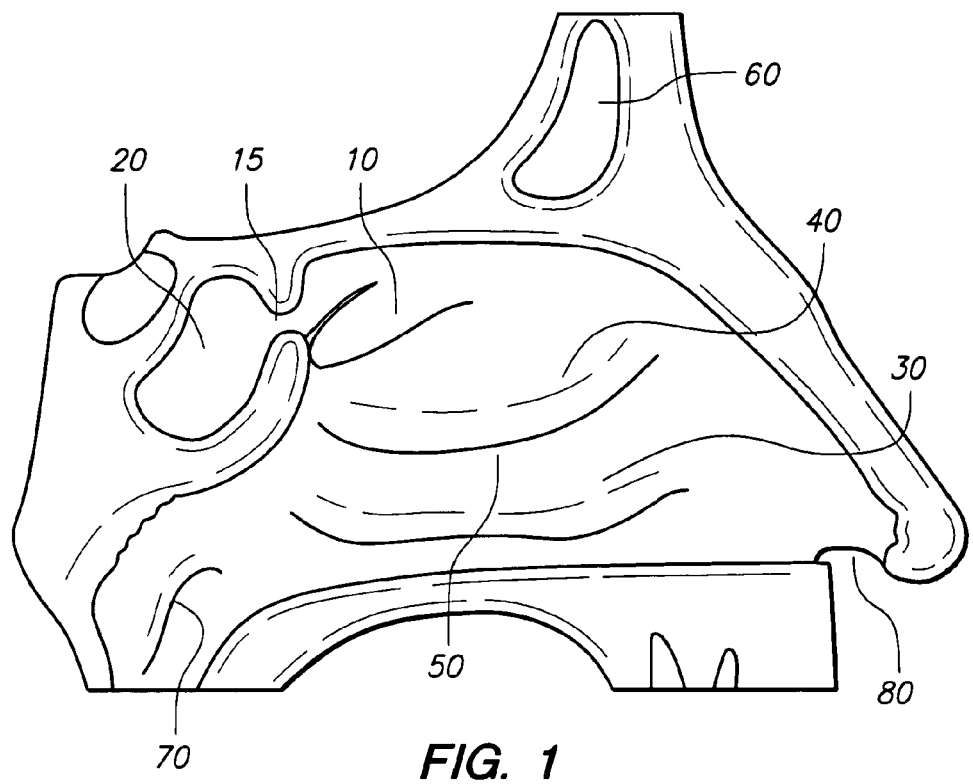
FIG. 1 is a cross sectional view of a human paranasal passageway showing the superior, middle, and inferior turbinates and their positioning in relation the frontal and sphenoid nasal sinuses.

Referring first to FIG. 1, a cross section of a patient's paranasal passageway is shown with the superior turbinate 10 near the ostium 15 of the sphenoid sinus 20, an inferior turbinate 30, a middle turbinate 40 shown with a middle meatus 50 therebetween, a frontal sinus 60, and the Eustachian tube opening 70. The ostium (not shown) of the frontal sinus 60 is obstructed in this illustration by the middle turbinate 40. The inferior turbinates 30 are the largest turbinates, being about 3 inches in length, and are responsible for the majority of airflow direction, humidification, heating, and filtering of air inhaled through the nose. The middle turbinates 40 are smaller and are about two inches in length. The middle turbinates 40 project downwards over the openings of the maxillary and ethmoid sinuses, and act as buffers to protect the sinuses from coming in direct contact with pressurized nasal airflow. Most inhaled airflow travels between the inferior turbinate and the middle turbinate 40. The superior turbinates 10 are smaller structures, connected to the middle turbinates by nerve-endings, and serve to protect the olfactory bulb.

During nasal surgery, surgical devices may be inserted through the nasal opening 80 of the nose to perform corrective surgical operations. Such devices can damage portions of the inferior 30 and middle turbinates 40 as the user of the surgical devices navigates the surgical devices through the paranasal passageway to the surgical site. The anterior portion of the middle turbinate 40 is vulnerable to trauma by surgical devices in most types of sinusitis surgeries, and in particular, when the surgery involves opening the frontal sinus ostium and/or navigating surgical devices through the frontal sinus ostium.

Figure 2:
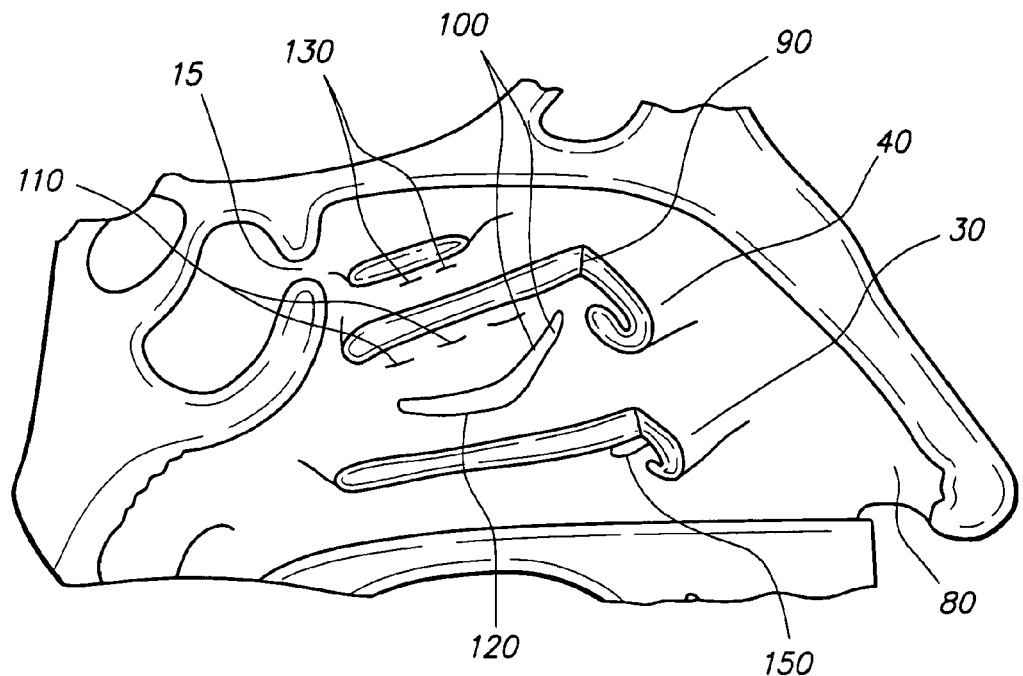
FIG. 2 is a cross sectional view of a human nasal passageway showing the superior, middle, and inferior turbinates in cross section, as well as their positioning in relation the frontal and sphenoid nasal sinus ostia.

FIG. 2 shows the view of a patient's paranasal passageway of FIG. 1, but with portions of the superior 10, middle 40 and inferior 30 turbinates shown in cross section to more clearly illustrate the location of sinus ostia and other nasal ostia with respect to the nasal turbinates: The middle turbinate 40 obscures the frontal sinus ostia 90 as well as openings 100 to the anterior ethmoid cells, openings 110 to the middle ethmoid cells, and the maxillary sinus ostium 120, thus increasing the chances of trauma to the middle turbinate 40 when access to these openings, particularly the frontal sinus ostium, is needed during surgery. The superior turbinate 10 is vulnerable to trauma by surgical devices particularly when the openings 130 of the posterior ethmoid cells or the sphenoid ostium 15 must be navigated by surgical devices or are the site of the surgical procedure, such as enlarging the sphenoid ostia by a balloon catheter, for example. The inferior turbinate 30 is most likely to be damaged during procedures involving the nasalcranial duct 150 located behind the inferior turbinate 30.

Figure 3A:
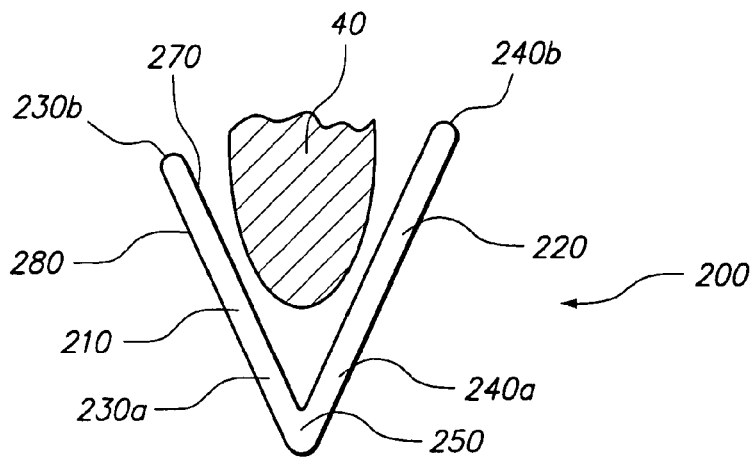
FIG. 3a-d are top, front, perspective and side views respectively of an embodiment of a turbinate protector in accordance with the invention.
Figure 3B:
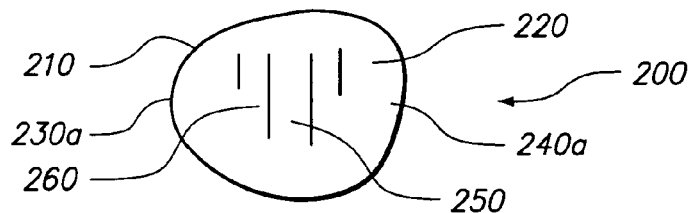
Figure 3C:
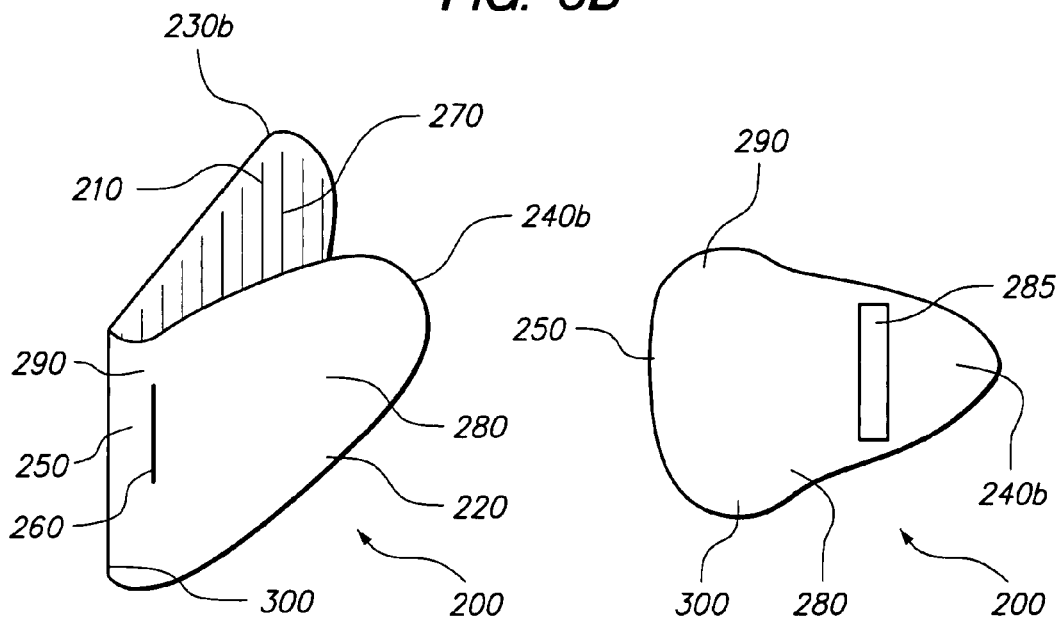
Figure 3D:
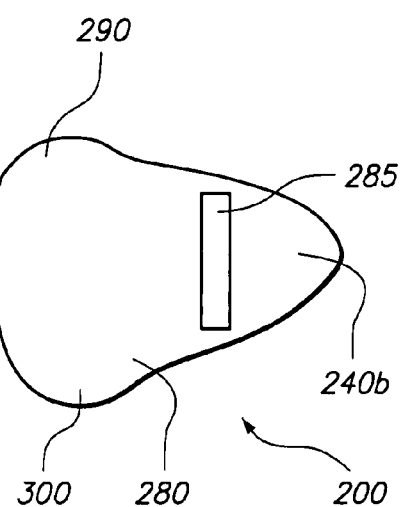

Referring now to FIGS. 3a-d, one embodiment of a turbinate protector 200 is shown in accordance with the invention. FIGS. 3a and 3b respectively provide a top view and a front view of a turbinate protector 200 configured to help protect the middle turbinate from trauma by surgical instruments during a sinus surgical procedure. FIGS. 3c and 3d are respectively a perspective view and a side view of the turbinate protector 200 of FIG. 3a and FIG. 3b. Turbinate protector 200 comprises a first substantially planar portion, member, wing or flap 210 and a second substantially planar portion, member, wing or flap 220. The first and second substantially planar portions 210, 220 each have a proximal end portion 230a, 240a respectively, and a distal end portion 230b and 240b respectively. The proximal end portions 230a and 240a of portions 210 and 220 are joined or connected to one another by a resilient, bendable or malleable portion, bridge or connecting region 250.

FIG. 3a is shown with the middle turbinate 40 of a patient positioned between portions 210, 220 of turbinate protector 200. When positioned in the paranasal cavity, the first and second portions 210, 220 of turbinate protector 200 are configured to be positioned adjacent to the opposite the sides of the middle turbinate 40 and protect the sides (i.e. left or right side) of the turbinate. The malleable portion 250 is configured to protect the anterior portion and/or inferior portion of the middle turbinate 40. The bridge portion 250 and side portions 210, 220 thus define or provide a "tent"-shaped protector for the turbinate 40, with portions 210, 220 serving as protecting members or elements for the sides of turbinate, and with bridge or connector 250 serving as a protecting member or element for anterior and/or inferior portions of turbinate 40. Portion 250 defines a rounded, atraumatic surface that avoids or minimizes damage or irritation to tissue to which portion 250 may contact. Distal end portions 230b, 240b are also atraumatic and may be rounded in shape as shown more particularly in FIGS. 3c and 3d, to provide atraumatic surfaces.

While the turbinate protector 200 is shown in association with the middle turbinate 40, it should be understood that the invention may be used to protect other turbinates or other portions of the paranasal cavity. Thus, while the first and second portions 210 and 220 are shown as having generally the same length or size with respect to each other, the planar portions 210 and 220, as well as the bendable portion 250, may be varied in size and shape according to the type or shape of the turbinate to be protected.

In some embodiments of the invention, the protector 200 comprises at least one crease, slot or indent 260 (FIG. 3b) proximate to the bridge portion 250. The creases 260 are configured to increase the resiliency or malleability of portion 250 and aid the user or surgeon in placing the protector 200 over the turbinate with a surgical device such as a pair of forceps. The crease(s) 260 may also be configured to move, bend or otherwise reconfigure the substantially planar portions 210 and 220 to their respective left or right sides of the turbinate being protected.

FIG. 3c illustrates the overall "winged" shape of the turbinate protector 200, with the distal end portions 230b and 240b of the substantially flat portions 210 and 220 angled away from each other. The angle or dihedral defined by portions 210, 220 and the malleable portion 250 may vary depending on the shape of the turbinate to be protected. In general, the angle defined by portions 210, 220 and the malleable portion 250 may range, for example, from about 120 degrees to about 10 degrees. More preferably, then angle will range from about 60 degrees to about 20 degrees.

The turbinate protector 200 comprises an inner side 270 and outer side surfaces 280. The inner side surface 270 is configured to contact the middle turbinate 40, and the outer side 280 is configured to disperse or deflect forces generated by the impact of a surgical instrument (not shown) when the surgical instrument comes in contact the turbinate protector 200. By dispersing the forces generated by the impact of a surgical instrument, the turbinate protector 200 shields the middle turbinate 40 from direct contact with the surgical instrument and prevents or reduces the amount of trauma that would otherwise be caused by the surgical instrument. Inner side 270 surface may further comprise a coating of a biocompatible (and, optionally, biodegradable) adhesive to aid in the positioning and securing of the turbinate protector 200 on the turbinate 40. Such biocompatible adhesives that may be used include but are not limited to cyanoacrylates, collagen-, carbohydrate- and/or protein-based adhesives.

In some embodiments turbinate protector 200 may include one or more radio-opaque markers 285 to allow the surgeon user to visualize and position the turbinate protector 200 by fluoroscopy or other x-ray techniques during surgery. The marker 285 may alternatively be made of electromagnetic, piezoelectric or magnetic materials, depending of the visual navigational technique being utilized during the surgical procedure.

Turbinate protector 200 may be manufactured from various resilient and/or malleable materials which allow the turbinate protector to be bent or formed around a portion of the middle turbinate most susceptible to trauma by surgical instruments. In general, the turbinate protectors of the invention are made of thin, resilient polymeric materials capable of dispersing force and pressure over a larger area to aid in the reduction of friction and/or chafing from surgical instruments. Suitable biocompatible material(s) that can be used for construction of a turbinate protecting device include but are not limited to metals e.g. malleable stainless steel, fully annealed stainless steel, copper, aluminum, titanium, nickel-titanium alloy (e.g., Nitinol), etc.; polymers e.g., polyether block amides (e.g., Pebax), polyether ether ketone (PEEK), Nylon, polyethylene, polyimide, polyurethane, polytetrafluoroethylene (PTFE), etc., or bioabsorbable materials such as polymers based on polycaprolactone, polyglycolic acid (PGA), polylactic acid (PLA), or copolymers of PGA and PLA. In certain embodiments the bridge portion 20 may comprise a malleable material such as annealed stainless steel, while wing portions 210, 220 are made of a resilient material.

The turbinate protector 200 is anatomically shaped and can be placed over a variety of turbinate sizes and shapes, including pneumatized turbinates. The embodiments of the turbinate protectors disclosed herein are especially configured for the middle turbinate when treating the maxillary, frontal, and/or sphenoid sinuses via balloon sinuplasty. As noted above, the configuration of the turbinate protectors of the invention may be varied as required to protect different turbinates or turbinate surfaces.

Figure 4:
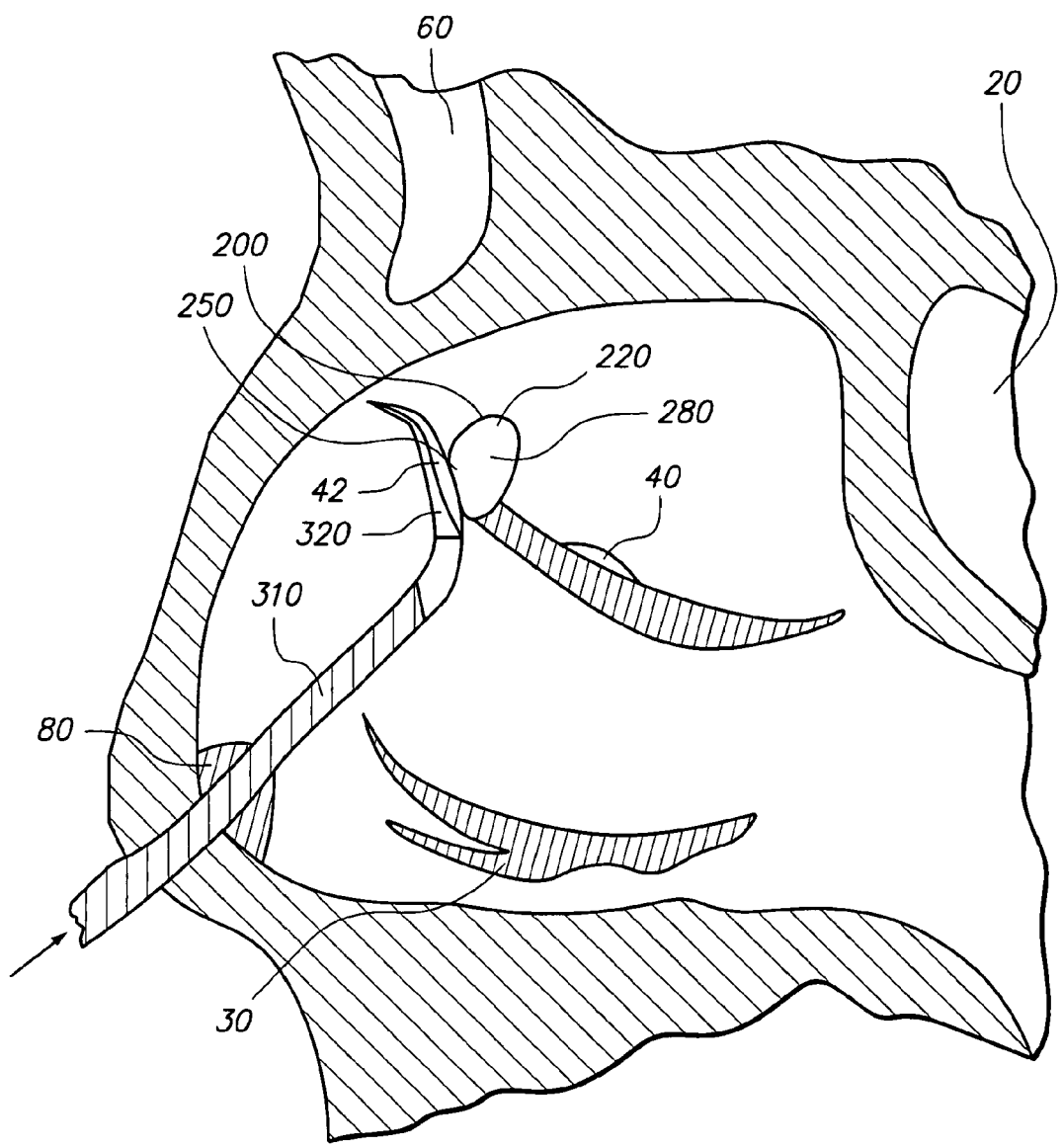
FIG. 4 is a cross-sectional view of a human nasal passageway showing one embodiment of a turbinate protector positioned over the middle turbinate of a patient in accordance with the invention.

FIG. 4 is a cross-sectional view of a human nasal passageway showing one embodiment of a turbinate protector positioned over the middle turbninate 40 of a patient in accordance with methods of the invention, Prior to sinus surgery of the maxillary sinus, the turbinate protector 200 is introduced through the nasal passageway through a nostril and positioned on a section of the anterior/inferior portion of the middle turbinate 40. After positioning the turbinate protector 200, a guide catheter 310 is introduced into the patient via a nostril and is positioned in the maxillary sinus ostium (not shown), located near the uncinate process 42 of the patient. The turbinate protector 200 protects the middle turbinate 40 from damage from the distal end portion 320 of the guide catheter that may otherwise harm the middle turbinate. The turbinate protector 200 also avoids damage to the turbinate from other surgical instruments, guide wires, endoscopic imaging tools and the like.

Figure 5:
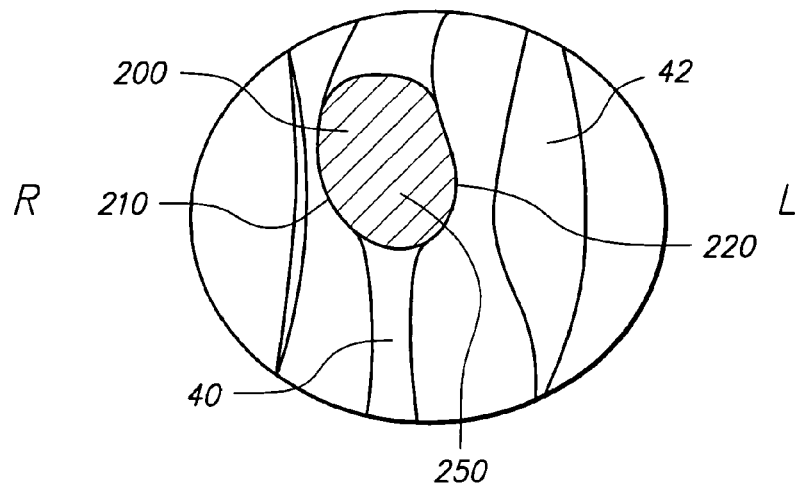
FIG. 5 is an endoscopic view of a human nasal passageway showing a middle turbinate and the region of the middle, turbinate that would be protected by the turbinate protector and turbinate protecting methods of the invention.

FIG. 5 is an endoscopic view of the human nasal passageway of FIG. 4, showing turbinate protector 200 protecting a section of the anterior/inferior portion the middle turbinate. 40. Similar to the front view shown in FIG. 3b, the bendable portion 250 of the turbinate protector is shown in FIG. 5 as well as portions 210 and 220. The view provided by FIG. 5 illustrates the close proximity of the uncinate process 42 to the middle turbinate 40.

Figure 6A:
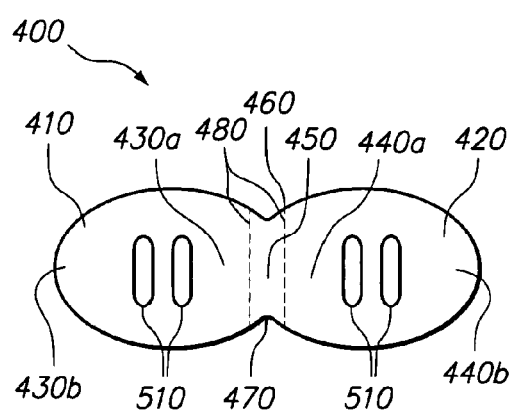
FIG. 6a-c show one embodiment of a turbinate protector respectively in an extended position, in a folded position, and positioned for grasping with forceps.
Figure 6B:
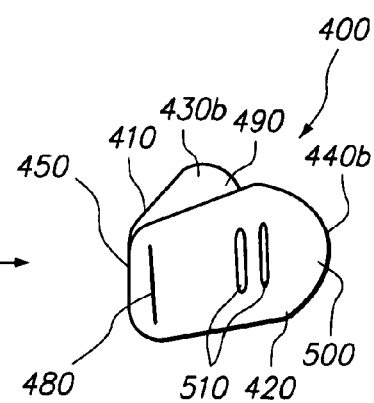
Figure 6C:
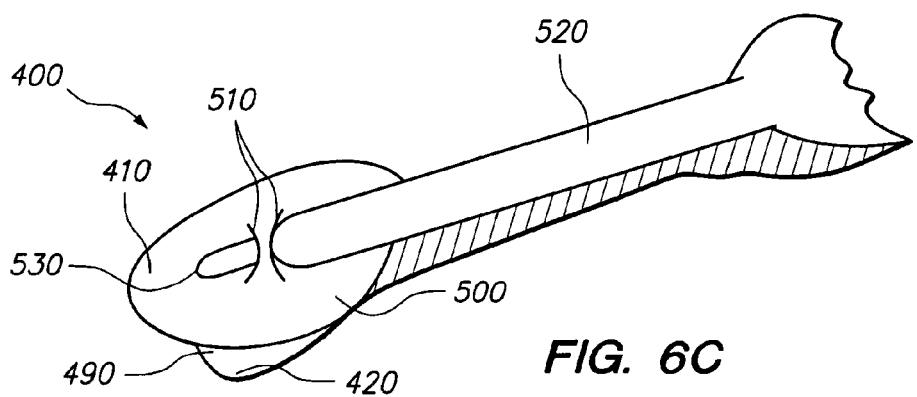

Referring now to FIGS. 6a-c, there is shown another embodiment of a turbinate protector 400 in accordance with the invention. FIG. 6a is a front view of a turbinate protector 400 shown in an extended or flat position. FIG. 6b is a perspective view of the turbinate protector 400 of FIG. 6a shown in a folded position. FIG. 6c shows the turbinate protector 400 being held by forceps. Turbinate protector 400 may be manufactured from a substantially flat sheet of material, which can then be bent, creased or folded into the configuration shown in FIG. 6b. The turbinate protector 400 can be easily and conveniently stored in a flat or extended position before use. Materials useful in the manufacturing of turbinate 400 may include but are not limited to PEEK, nylon, PEBAX, PTFE, annealed stainless steel, NITINOL, or biaoabsorbable materials, such as polymers based on polycaprolactone, PGA, PLA, or copolymers of PGA and PLA. Turbinate protector 400 comprises first and second substantially planar wing-like portions or members 410 and 420 respectively, each having a proximal end portion 430a, 440a, and a distal end portion 430b and 440b, wherein the proximal end portions 430a and 440a of the substantially planar portions 410 and 420 are connected to one another by a resilient, bendable or malleable bridge or connecting portion 450. While the first and second portions 410 and 420 are shown as having the same relative size and shape, flat portions 410 and 420 as well as bendable portion 450 may also be of different (i.e. unequal) sizes or shapes depending on the type or shape of the turbinate to be protected. The bendable or foldable portion 450 further comprises a top portion 460 and bottom portion 470 with at least one crease or fold line(s) 480 extending between the top 460 and 470 bottom portions, to allow the turbinate protector 400 to be folded along the crease 480 as shown in FIG. 6b. In some embodiments, the bendable 450 portion of the turbinate protector 400 comprises a plurality of crease or fold lines 480 to conform more precisely to a particular sinus turbinate to be protected. The crease(s) 480 may also be configured to move and/or bend the substantially planar portions 410 and 420 to their respective left or right sides of the turbinate to be protected.

Turbinate protector 400 further comprises an inner side surface 490 and outer side surface 500, the inner side surface 490 configured to contact the turbinate to be protected and the outer side 500 configured to disperse the forces generated by the impact of a surgical instrument when the surgical instrument comes in contact the turbinate protector 400. Inner side 490 surface may further comprise a coating of a biodegradable adhesive to aid in the positioning and temporary securement of the turbinate protector on the turbinate.

The turbinate protector 400 may include one or more openings 510 on flat portion 410 and a corresponding opening or openings (not shown) on flat portion 420. Openings 510 are structured to allow forceps 520 or other surgical device to be inserted into openings 510 to allow positioning of the turbinate protector 400 on a turbinate. In the embodiment shown in FIG. 6c, there are two openings or slits 510 on each of portions 410 and 420, thus allowing the distal ends 530 of the forceps 520 to remain on the outer side surface 500 of the turbinate protector 400. The openings 510 may extend through portions 410, 420 and inner surface 490, In certain embodiments, the openings 510 do not penetrate the inner surface 490 at all. Forceps 520, when inserted into openings 510, may be used to exert an opening force on portions 410, 420 such that portions 410, 420 move apart in a "clam-like" motion, with distal end portions 430b, 440b undergoing the greatest movement, allowing the protector 400 to be easily positioned over a turbinate. Removing the opening force from turbinate protector by releasing forceps 520 and removing forceps 520 from openings 510, results in portions 410, 420 moving together or closing, to secure the turbinate between the protecting portions 410, 420 and bridge 450.

Turbinate protector 400 may include one or more radio-opaque markers (not shown) or markers comprising magnetic material to allow the surgeon user to visualize and position the turbinate protector 400 by fluoroscopy or other x-ray techniques during surgery.

Figure 7A:
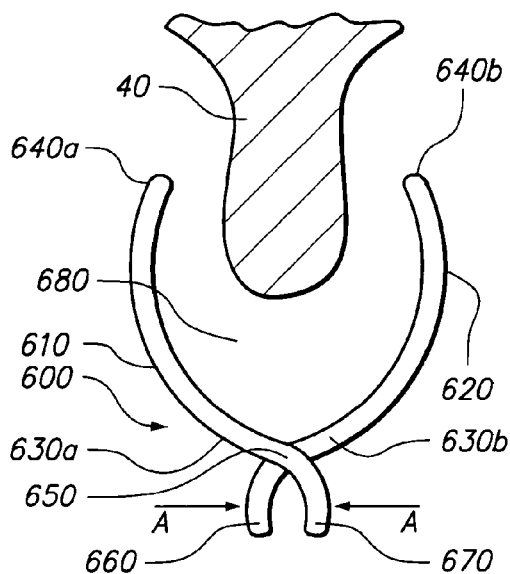
FIGS. 7a and 7b respectively show side views of another embodiment of a turbinate protector in opened and closed positions.
Figure 7B:
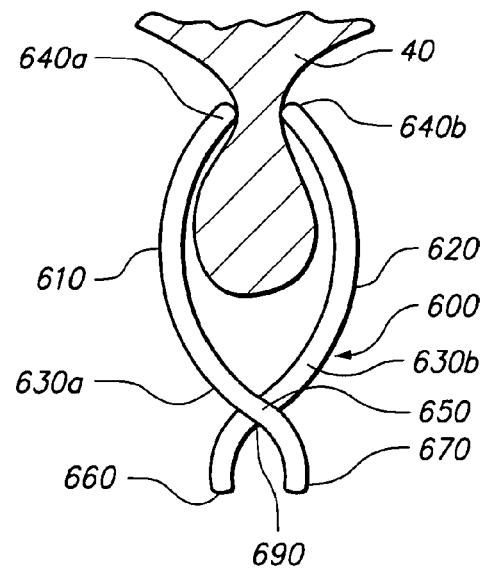

FIG. 7a and FIG. 7b show yet another embodiment of a turbinate protector 600 in accordance with the invention, wherein FIG. 7a shows turbinate protector 600 in a forced or open position, and FIG. 7b shows protector 600 in a relaxed or closed position. Turbinate protector 600 includes first and second protecting elements or portions 610, 620 having proximal end portions 630a, 630b respectively, and distal end portions 640a, 640b respectively. First and second portions 610, 620 are joined or connected by a bridge or connecting portion or section 650. Also joined to connecting section 250 are opening and closing control elements 660, 670.

Connecting section 650 serves as a mechanical interface between closure or control elements 660, 670 and portions 610, 620. Connecting section 650 and closure elements 660, 670 are mechanically coupled or interfaced with portions 610, 620 via connecting or bridge portion 650. Closure elements 660, 670 are structured and configured such that, by application of forces indicated by arrows "A" (FIG. 7a) from forceps (not shown) or other instrument, portions 610, 620 move apart from each other in a "pincer-like" motion to define an opening 680 (FIG. 7a) that allows turbinate 40 to fit between portions 610, 620 and into opening 680. When the forces indicated by arrows "A" are removed by releasing elements 660, 670, the turbinate protector 600 returns to a relaxed or closed position with portions 610, 620 surrounding and protecting turbinate 40. Connecting or bridge portion 650 may comprise a resilient material, with portions 610, 620 and elements 660, 670 joined to bridge portion 650 and structured and configured such that application of forces "A" results in suitable flexion of connecting region 650 to communicate forces "A" to portions 610, 620 such that portions undergo an opening motion, and such that release or removal of forces "A" results in closing of portions 610, 620 as shown in FIG. 7a and FIG. 7b. Opening forces "A" may be applied, for example, by grasping and squeezing elements 660, 670 with forceps or like instrument (not shown), and releasing the forceps from elements 660, 670 removes forces "A".

In certain embodiments a pivot point mechanical assembly 690 (FIG. 7b) may be located at connecting region 650. Mechanical interface 690 may comprise a spring and pin assembly configured to transfer force from elements 670, 680 to portions 610, 620 to provide opening and closing as described above. Turbinate protector 600 may include radioopaque markings or indicia as described above to aid the user in positioning turbinate protector 600. The inner surface (not shown) of portions 610, 620 may include a bioadhesive to facilitate temporary fixation of turbinate protector to turbinate 40 as described above.

Figure 8A:
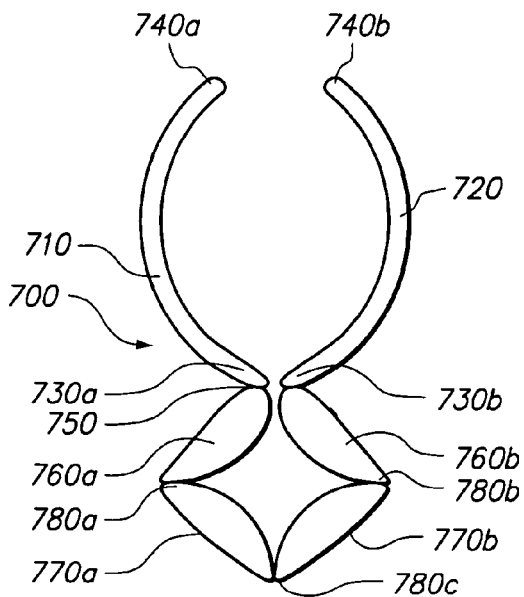
FIGS. 8a and 8b respectively show another embodiment of a turbinate protector in closed and open positions.
Figure 8B:
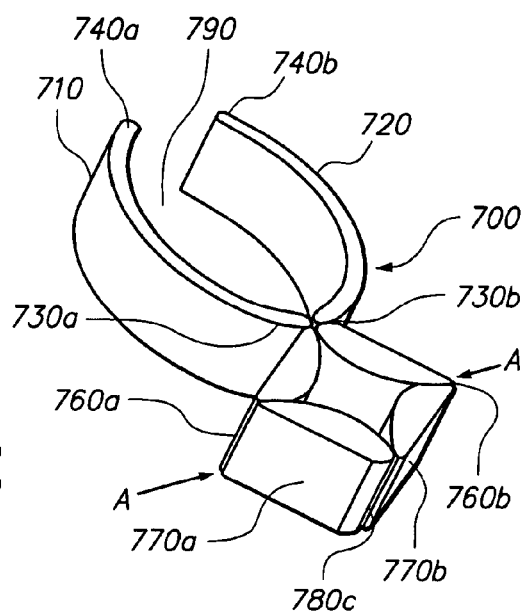

Referring now to FIGS. 8a and 8b, there is shown another embodiment of a turbinate protector 700 in accordance with the invention. FIG. 8a shows turbinate protector 700 in a closed or relaxed position, and FIG. 8b shows the turbinate protector 700 in an open or extended position.

Turbinate protector 700 includes first and second protecting elements or portions 710, 720 having proximal end portions 730a, 730b respectively, and distal end portions 740a, 740b respectively: A bridge or connecting region or section 750 joins first and second portions 710, 720 together. A first pair of control elements or segments 760a, 760b are joined to connecting region 750. A second pair of control elements or segments 770a, 770b are respectively joined to the first pair of segments 760a, 760b by connecting regions or sections 780a, 780b (FIG. 8a), such that segments 760a and 770a are joined by section 780a, and segments 760b and 770b are joined by section 780b. In certain embodiments, segments 770 and 770b may be joined together by section 780c.

Connecting region 750 is flexible or resilient in nature such that connecting region 750 is mechanically interfaced with portions 710, 720 and with segments 760a, 760b. Connecting regions 780a, 780b and 780c likewise are flexible or resilient and provide a mechanical coupling or interface between segments 770a, 770b and segments 760a, 770b respectively. Connecting regions 750, 780a, 780b and 780c and segments 760a, 760b, 770a, 770b are thus mechanically coupled to portions 710, 720 via bridge or connecting region 750. Connecting regions 750, 780a, 780b and 780c and segments 760a, 760b, 770a, 770b are structured and configured such that application of an inward pressure or force as shown by arrows "A" (FIG. 7b) on segments 760a, 760b, 770a, 770b and/or regions 780a, 780b will impart or provide an opening force to portions 710, 720, and release of the pressure or force "A" from segments 760a, 760b, 770a, 770b and/or regions 780a, 780b results in a closing motion by portions 710, 720. When in the open position as shown in FIG. 8b, portions 710, 720 define an opening 790 that allows a turbinate (not shown) to fit between portions 710, 720. In the closed position shown in FIG. 8b, the turbinate is secured between portions 710 and 720. Introduction and removal of forces "A" may be achieved by respectively grasping and releasing segments 760a, 760b, 770a, 770b with forceps or other instrument.

In certain embodiments pivot point mechanical assemblies, such as pin and spring assembly (not shown), may be located at connecting regions 750, 780a and 780b to provide for opening and closing of portions 710, 720 in the manner described above. The inner surface (not shown) of portions 710, 720 may include a bioadhesive to facilitate adherence to the turbinate as described above.

Figure 9:
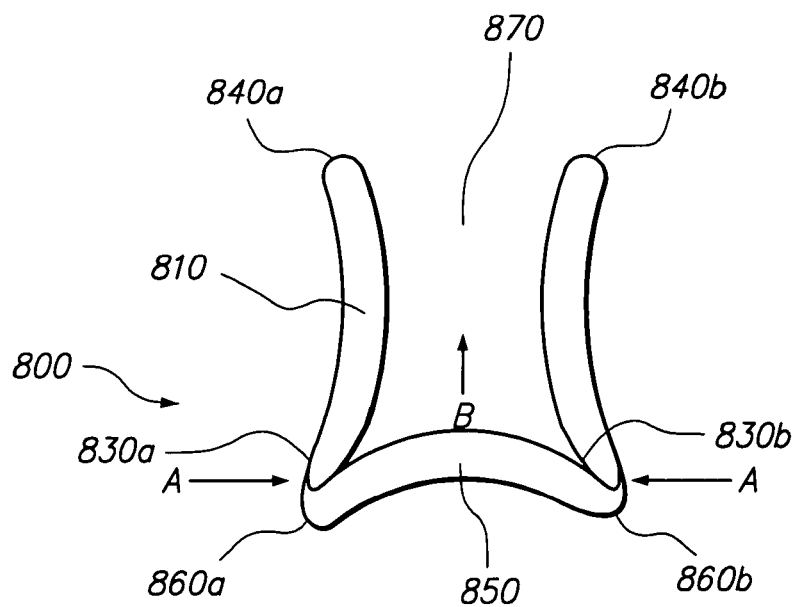
FIG. 9 is a side view of still another embodiment of a turbinate protector in accordance with the invention.

FIG. 9 provides a top view of still another embodiment of a turbinate protector 800 in accordance with the invention. The turbinate protector 800 includes protecting portions or sections 810, 820 each having proximal end portions 830a, 830b respectively, and distal end portions 840a, 840b respectively. A curved or arcuate-shaped flexible bridge or connector 850 is coupled to proximal end portions 830a, 830b of first and second portions 810, 820 by first and second connecting regions 860a, 860b. The flexible connector 850 is thus mechanically interfaced to portions 810, 820 by regions 860a, 860b.

The turbinate protector 800 of FIG. 9 is shown in a closed position. Application of an opening force as indicated by arrows "A" on connector 850, using forceps or other instrument as described above, causes connector 850 to flex or bend in the direction indicated by arrow "B", which imparts an opening motion to portions 810, 820, such that portions 810, 820 move apart to an opened position (not shown). In the opened position, a turbinate (not shown) can access opening or cavity 870, and when in the closed position, the turbinate protector 800 is held in position on the turbinate by portions 810, 820.

Figure 10:
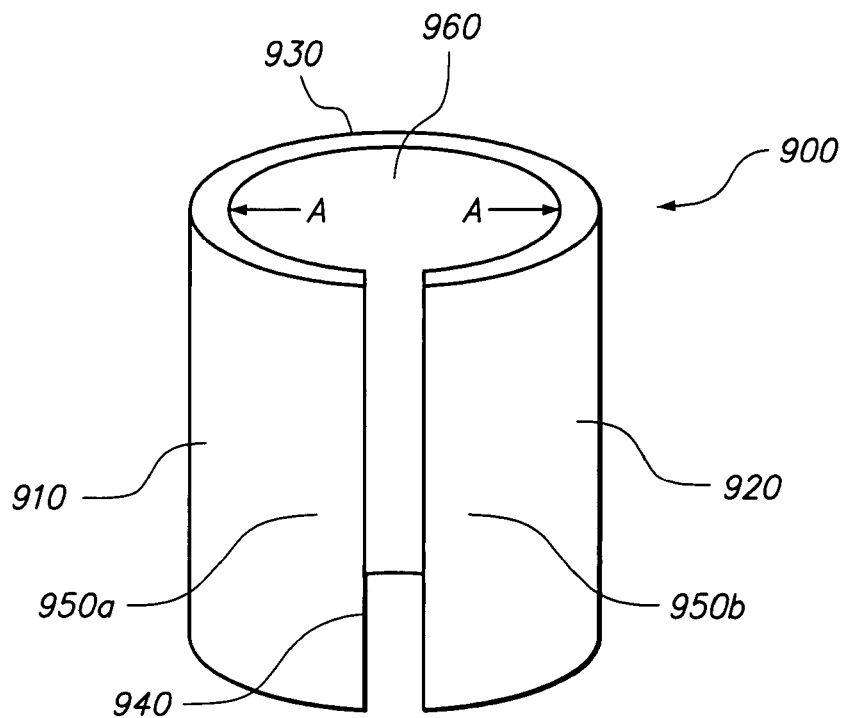
FIG. 10 is a perspective view of yet another embodiment of a turbinate protector in accordance with the invention.

FIG. 10 shows another embodiment of a turbinate protector 900 in accordance with the invention. The turbinate protector 900 comprises protecting portions or sections 910, 920, and a curved or arcuate-shaped flexible bridge or connector 930 joined to portions 910, 920. In the embodiment of FIG. 10, portions 910, 920 and connecting region 930 define a contiguous cylindrical shape with a slot 940 between the distal end portions 950a, 950b of portions 910, 920 respectively. In the embodiment of FIG. 10, application of an opening force or forces represented by arrows "A" results in an opening motions such that the distal end portions 950a, 950b move apart and widen slot 940 so that a turbinate (not shown) can fit through slot 940 and into opening 960 between portions 910, 920. Removal of the opening force results in a closing motion such that portions 910, 920 move together, so that the turbinate is secured within opening by end portions 950a, 950b. The opening force may be applied to the turbinate protector 900 by inserting forceps or like instrument (not shown) into opening 960 and exerting an opening force as indicated by arrows "A".

Figure 11:
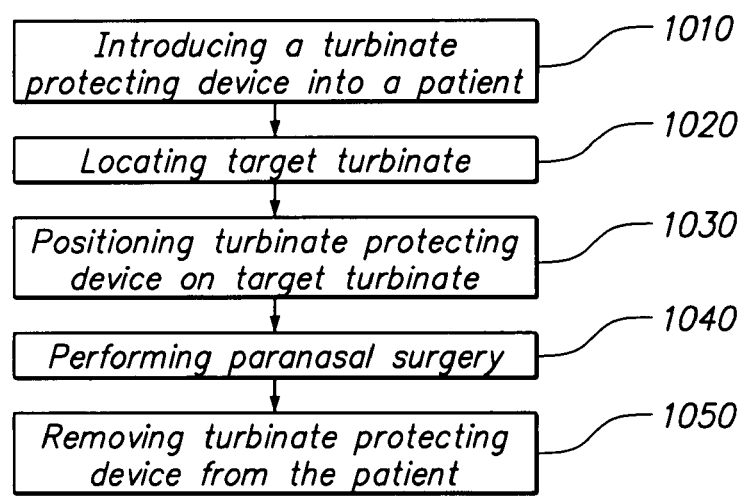
FIG. 11 is a flow chart showing a method for protecting a turbinate in accordance with the invention.

Referring now to FIG. 11, there is shown a flow chart illustrating steps that may be performed according to an embodiment of a method of the present invention. In event 1010, introducing a turbinate protecting device into a patient is carried out. The introducing may comprise, for example, inserting the turbinate protector through the nostril 80 (FIG. 2) and nasal passage of a patient using forceps 520 (FIG. 6c) or other instrument.

In event 1020, a target turbinate is located. The locating may comprise, for example, visualizing the selected or target turbinate via endoscopic imaging.

In event 1030, the turbinate protector is positioned on the target turbinate. The positioning may comprise, for example, positioning first protecting portion 210 (FIG. 3a-3c) of turbinate protector 200 adjacent or proximate to a first side of turbinate 40, positioning second protecting portion 220 of turbinate protector 200 adjacent or proximate to a second side of turbinate 40, and positioning connecting or bridge region 250 adjacent or proximate to the anterior or inferior portion of turbinate 40. The positioning may further comprise contacting turbinate 40 with inside surface 270, which may optionally include a bioadhesive as described above, such that the positioning further comprises securing the inside surface of the turbinate protector to the turbinate with a bioadhesive located on the inner surface. The positioning may be carried out using forceps 520 (FIG. 6) or like surgical instrument.

In certain embodiments such as those illustrated in FIGS. 6a-6c, the positioning 1030 may comprise moving the first and second portions 410, 420 of the turbinate protector 400 to an open position, positioning the target turbinate between the first and second portions 410, 420, and moving the first and second portions 410, 420 to a closed position. The opening of portions 410, 420 may, in certain embodiments, comprise applying an opening force to portions 410, 420, and the closing may comprise removing the opening force from portions 410, 420. In other embodiments the opening of portions 410, 420 may comprise applying an opening force bridge portion 450, and the closing of portions 410, 420 may comprise removing the opening force from the bridge portion 450.

More particularly, the positioning may comprise moving the first and second portions 410, 420 of the turbinate protector 400 to an open position, positioning the target turbinate between the first and second portions 410, 420, positioning the first portion 410 adjacent to a first side of the turbinate, positioning the second. portion 420 adjacent to a second side of the target turbinate, positioning the bridge portion 450 adjacent to an anterior or inferior portion of the turbinate, and moving the first and second portions 410, 420 to the closed position.

In another embodiment, the positioning 1030 may comprise applying an opening force to control elements 660, 670 (FIG. 7a) of turbinate protector 600 to open or move portions 610, 620 apart, positioning the turbinate 40 within the opening 680, positioning first portion 610 of turbinate protector 600 adjacent or proximate to a first side of turbinate 40, positioning second portion 620 of turbinate protector 600 adjacent or proximate to a second side of turbinate 40, positioning connecting or bridge region 650 adjacent or proximate to the anterior or inferior portion of turbinate 40, and removing the opening force from control elements 610, 620. The positioning may further comprise contacting an inner surface of protector 600 with turbinate 40. Applying the opening force to control elements 660, 620 may comprise grasping control elements 660, 670 with forceps, and removing the force from control elements 660, 670 may comprise releasing control elements 660, 670.

In event 1040, paranasal surgery is performed. Performing paranasal surgery may comprise carrying out a variety of surgical techniques or operations, including FESS and FTSI surgeries as described above.

In event 1050, the turbinate protecting device is removed from the turbinate and the patient. The removing in many embodiments may comprise opening the first and second portions of the protector to release the turbinate, and withdrawing the turbinate protector from the patient nasal cavity via the nostril using a suitable surgical instrument. Alternatively, if the turbinate protector is made from a bioabsorbable polymer, it may be left in place and allowed to dissolve over time.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A turbinate protector comprising:
    (a) a first protecting portion;
    (b) a second protecting portion; and
    (c) a bridge portion joined to the first and second protecting portions;
    wherein the turbinate protector is sized and configured to fit on a turbinate, and wherein the first and second protecting portions each includes a proximal end portion, and each of the proximal end portions is joined to the bridge portion.

2. The turbinate protector of claim 1, wherein the first protecting portion is structured and configured to protect a first side of a turbinate, the second protecting portion is structured and configured to protect a second side of a turbinate, and the bridge portion is structured and configured to protect an anterior or inferior portion of the turbinate.

3. The turbinate protector of claim 1, wherein the first and second protecting portions are substantially planar in shape.

4. The turbinate protector of claim 3, wherein the first and second protecting portions each include a distal end portion, the distal end portions each having a rounded shape, the rounded shapes defining atraumatic surfaces.

5. The turbinate protector of claim 1, wherein the bridge portion is resilient and the first and second protecting portions are movable with respect to the bridge portion.

6. The turbinate protector of claim 5, wherein the first and second protecting portions are reversibly movable from an open position to a closed position.

7. The turbinate protector of claim 6, wherein the first and second protecting portions are movable to an open position by application of an opening force to the first and second protecting portions, and movable to a closed position by removal of the opening force from the first and second protecting portions.

8. The turbinate protector of claim 6, wherein the first and second protecting portions are movable to an open position by application of an opening force to the bridge portion, and movable to a closed position by removal of the opening force from the bridge portion.

9. The turbinate protector of claim 1, wherein the first and second protecting portions and bridge portion are joined together in a configuration that defines an angle between the first and second protecting portions of between about 25° and about 45°.

10. The turbinate protector of claim 1, wherein the bridge portion further comprises at least one crease, the crease configured to increase resiliency of the bridge portion.

11. The turbinate protector of claim 1, wherein the first and second protecting portions and bridge portion further comprise an inner surface structured and configured to contact a turbinate.

12. The turbinate protector of claim 11, wherein the inner surface includes a biocompatible adhesive.

13. The turbinate protector of claim 1, further comprising at least one radio-opaque marker on said turbinate protector.

14. The turbinate protector of claim 1, wherein the first and second protecting portions and bridge portion further comprise an outer surface structured and configured to deflect a surgical instrument.

15. The turbinate protector of claim 1, wherein the first and second protecting portions each include at least one slot structure and configured to facilitate grasping of the first and second portions by a surgical instrument.

16. The turbinate protector of claim 1, further comprising first and second control elements, wherein the first and second control elements are structured and configured such that application of an opening force to the first and second control elements causes the first and second protecting portions to move apart to an open position, and removal of the opening force from the first and second control elements results in the first and second portions moving together to a closed position.

17. The turbinate protector of claim 16, wherein the first and second control elements are structured and configured such that application of an opening force to the first and second control elements causes distal end portions of the first and second protecting portions to move apart to an open position, and removal of the opening force from the first and second control elements results in the distal end portions of the first and second portions moving together to a closed position.

18. The turbinate protector of claim 16, wherein the first control element comprises first and second control segments, and the second control element comprises first and second control segments, the first and second control segments of each control element mechanically coupled to each other.

19. A turbinate protector comprising:
(a) a first protecting portion;
(b) a second protecting portion; and
(c) a bridge portion joined to each of the first and second protecting portions;
wherein the turbinate protector is sized and configured to fit on a turbinate;
wherein the first and second protecting portions and bridge portion each further comprise an inner surface that is structured and configured to contact a turbinate;
wherein the inner surface comprises a biocompatible adhesive.

20. A turbinate protector comprising:
(a) a first protecting portion;
(b) a second protecting portion; and
(c) a bridge portion joined to the first and second protecting portions;
wherein the turbinate protector is sized and configured to fit on a turbinate;
wherein the turbinate protector further comprises a first control element and a second control element;
wherein the first and second control elements are mechanically coupled to the first and second protecting portions through the bridge portion.

* * * * *